United States Patent [19]

Grinna et al.

[11] Patent Number: 5,284,756
[45] Date of Patent: Feb. 8, 1994

[54] HETERODIMERIC OSTEOGENIC FACTOR

[76] Inventors: Lynn Grinna, 1044 20th St., Santa Monica, Calif. 90403; Georgia Theofan, 3014 Sonoma St., Torrance, Calif. 90503; Thomas F. Parsons, 270 Renoak Way, Arcadia, Calif. 91006

[21] Appl. No.: 718,274

[22] Filed: Jun. 20, 1991

Related U.S. Application Data

[63] Continuation-in-part of Ser. No. 415,555, Oct. 4, 1989, Pat. No. 5,106,626, which is a continuation-in-part of Ser. No. 256,034, Oct. 11, 1988, abandoned.

[51] Int. Cl.$^5$ .............................................. C12P 21/06
[52] U.S. Cl. .................................. 435/69.4; 435/69.1; 435/172.3; 435/320.1; 536/23.5; 530/359; 530/399; 935/33; 935/66
[58] Field of Search .................... 536/27, 23.5; 435/320.1, 69.4, 69.1, 172.3, 240.2, 252.3, 252.33, 255; 530/417, 399

[56] References Cited

U.S. PATENT DOCUMENTS

| | | | |
|---|---|---|---|
| 3,458,397 | 7/1969 | Myers et al. | 195/2 |
| 4,294,753 | 10/1981 | Urist | 260/112.12 |
| 4,314,380 | 2/1982 | Miyata et al. | 3/1.9 |
| 4,394,370 | 7/1983 | Jefferies | 424/15 |
| 4,407,787 | 10/1983 | Stemberger | 424/2 |
| 4,430,760 | 2/1984 | Smestad | 3/1.9 |
| 4,434,094 | 2/1984 | Seyedin et al. | 260/112 R |
| 4,440,750 | 4/1984 | Glowacki et al. | 424/95 |
| 4,455,256 | 6/1984 | Urist | 260/112 R |
| 4,488,911 | 12/1984 | Luck et al. | 106/161 |
| 4,500,707 | 2/1985 | Caruthers et al. | 536/27 |
| 4,563,350 | 1/1986 | Nathan et al. | 424/95 |
| 4,563,489 | 1/1986 | Urist | 524/21 |

(List continued on next page.)

FOREIGN PATENT DOCUMENTS

| | | |
|---|---|---|
| 169016 | 1/1986 | European Pat. Off. . |
| 212474 | 3/1987 | European Pat. Off. . |
| 0349048 | 1/1990 | European Pat. Off. . |
| 409472 | 1/1991 | European Pat. Off. . |
| 416578 | 3/1991 | European Pat. Off. . |
| WO/8800205 | 1/1988 | PCT Int'l Appl. . |
| WO/8807548 | 10/1988 | PCT Int'l Appl. . |
| WO/8909787 | 10/1989 | PCT Int'l Appl. . |
| WO/8909788 | 10/1989 | PCT Int'l Appl. . |
| WO/8910409 | 11/1989 | PCT Int'l Appl. . |
| WO/9011366 | 10/1990 | PCT Int'l Appl. . |
| WO/9102744 | 3/1991 | PCT Int'l Appl. . |
| WO/9105802 | 5/1991 | PCT Int'l Appl. . |
| WO92/05199 | 4/1992 | PCT Int'l Appl. . |
| WO92/15323 | 9/1992 | PCT Int'l Appl. . |
| WO92/19262 | 11/1992 | PCT Int'l Appl. . |
| WO93/00432 | 1/1993 | PCT Int'l Appl. . |

OTHER PUBLICATIONS

Scopes in *Protein Purification*, pp. 186–191, 1987.

(List continued on next page.)

*Primary Examiner*—Robert J. Hill, Jr.
*Assistant Examiner*—Lorraine H. Spector
*Attorney, Agent, or Firm*—Marshall, O'Toole, Gerstein, Murray & Borun

[57] ABSTRACT

The present invention provides osteogenically active protein preparations comprising a heterodimer of P3 OF 31-34 subunit B and P3 OF 31-34 subunit D, which subunits are linked with at least one disulfide bond and methods for their preparation. The invention further provides cell lines transformed with nucleotide sequences encoding P3 OF 31-34 subunit B and P3 OF 31-34 subunit D and vectors comprising those sequences in operative association with an expression control sequence.

10 Claims, 13 Drawing Sheets

U.S. PATENT DOCUMENTS

| | | | |
|---|---|---|---|
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson et al. | 424/95 |
| 4,725,536 | 2/1988 | Fritsch et al. | 435/6 |
| 4,734,363 | 3/1988 | Dattagupta et al. | 435/91 |
| 4,757,006 | 7/1988 | Toole, Jr. et al. | 435/70 |
| 4,761,471 | 8/1988 | Urist . | |
| 4,774,228 | 9/1988 | Seyedin et al. | 514/21 |
| 4,774,322 | 9/1988 | Seyedin et al. | 530/353 |
| 4,789,732 | 12/1988 | Urist | 530/350 |
| 4,804,744 | 2/1989 | Sen | 530/350 |
| 4,863,899 | 9/1989 | Todaro | 514/9 |
| 4,877,864 | 10/1989 | Wang et al. | 530/324 |
| 4,952,404 | 8/1990 | Vallee et al. | 424/422 |
| 4,968,590 | 11/1990 | Kuberasampath et al. | 530/326 |
| 4,975,526 | 12/1990 | Kuberasampath et al. | 530/350 |
| 5,001,169 | 3/1991 | Nathan et al. | 523/113 |
| 5,002,770 | 3/1991 | Kuberasampath et al. | 424/423 |
| 5,011,691 | 4/1991 | Oppermann et al. | 424/423 |
| 5,013,649 | 5/1991 | Wang et al. | 435/69.1 |
| 5,017,486 | 5/1991 | Sawai et al. | 435/172.3 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,166,058 | 11/1992 | Wang et al. | 435/69.1 |
| 5,168,050 | 12/1992 | Hammonds, Jr. et al. | 435/69.1 |
| 5,182,365 | 1/1993 | Oppermann et al. | 530/326 |
| 5,187,076 | 2/1993 | Wozney et al. | 435/69.1 |

OTHER PUBLICATIONS

Amitani et al., *Calcif. Tiss. Res.*, 17, 139–150 (1975).
Assoian et al., *J. Biol. Chem.*, 258, 7155–7160 (1983).
Balland et al., *Biochimie*, 67, 725–736 (1985).
Bauer et al., *Clin. Ortho. Rel. Res.*, 154, 291–295 (1981).
Baylink et al., *J. Periodontal.*, 1, 43–49 (1979).
Bentz et al., *J. Bone and Mineral Res.*, 4, Supplement 1, p. S280, No. 650 (1989).
Bentz et al., *J. Cell. Biol.*, 107, 162a, No. 918 (1989).
Bentz, et al., *J. Biol. Chem.*, 265, pp. 5024–5029 (1990).
*Biotechnology Newswatch*, 9, No. 23, 1, 3 (Dec. 4, 1989).
Bitter et al., *Gene*, 32, 263–274 (1984).
Celeste et al., *Proc. Natl. Acad. Sci. USA*, 87, pp. 9843–9847 (1990).
Cepko et al., *Cell*, 37, 1053–1062 (1984).
Conover et al., *The Chemistry and Biology of Mineralized Connective Tissues*, 597–606, Elsevier (1981).
Drivdahl et al., *Proc. Soc. Exptl. Biol. Med.*, 168, 143–150 (1981).

Edge, *Nature*, 292, 756–762 (1981).
Farley et al., *Biochemistry*, 21, No. 14, 3502–3507 (1982).
Farley et al., *Biochemistry*, 21, No. 14, 3508–3513 (1982).
Gorman et al., *Mol. Cell. Biol.*, 2, 1044–1051 (1982).
Hanamura et al., *Clin. Ortho. Rel. Res.*, 148, 281–290 (1980).
Hanamura et al., *Clin. Ortho. Rel. Res.*, 153, 232–240 (1980).
Harakas, *Clin. Orthopaedics*, 188, 239–251 (1984).
Hauschka et al., *Proc. Natl. Acad. Sci.*, 72, 3925–3929 (1975).
Howard et al., *Metabolic Bone Disease Rel. Res.*, 2, 131–135 (1980).
Israel et al., *J. Cell. Biochem.*, Suppl. 15F, p. 168 (Abstract) (1991).
Kubersampath et al., *J. Biol. Chem.*, 265, pp. 13198–13205 (1990).
Luyten et al., *J. Biol. Chem.*, 264, 13377–13380 (1989).
Lyons et al., *Proc. Natl. Acad. Sci.*, 86, 4554–4558 (1989).
Maugh, *Science*, 217, 819 (1982).
Mbuyi et al., *Calcif. Tiss. Int.*, 34, 229–231 (1982).
Mizutani and Urist, *Clin. Ortho. Rel. Res.*, 171, 213–223 (1982).
Nogami et al., *Clin. Ortho. Rel. Res.*, 122, 307–314 (1977).
Özkaynak et al., *The EMBO Journal*, 9, pp. 2085–2093 (1990).
Price et al., *Proc. Natl. Acad. Sci.*, 73, 1447–1451 (1976).
Raisz et al., *New England J. Med.*, 309, No. 1, 29–35 (1983).
Raisz et al., *New England J. Med.*, 309, No. 2, 83–89 (1983).
Reddi, *Coll. Res.*, 1, 209–226 (1981).
Sampath et al., *Proc. Natl. Acad. Sci.*, 80, 6591–6595 (1983).
Sen et al., "Purification and Partial Characterization of a Novel Osteogenic Protein," pp. 201–220 in *Development and Diseases of Cartilage and Bone Matrix* (1987).
Seyedin et al., *Proc. Natl. Acad. Sci.*, 82, 2267–2271 (1985).
Takaoka et al., *Clin. Orthop. & Rel. Res.*, 148, 274 (1980).
Takaoka et al., *Clin. Orthop. & Rel. Res.*, 164, 265–270 (1982).

(List continued on next page.)

OTHER PUBLICATIONS

Takaoka et al., Purification of a Bone-Inducing Substance (Osteogenic Factor) from a Murine Osteosarcoma, *Biomed. Res.*, 2(5), 466–471 (1981).

Termine et al., "Mineral and Collagen-binding Proteins of Fetal Calf Bone," *Journal of Biological Chemistry*, No. 20, Issue of Oct. 25, pp. 10403–10408 (1981).

Termine et al., *Cell*, 26, 99–105 (1981).

Triffitt et al., *Calcif. Tiss. Res.*, 26, 155–161 (1978).

Urist et al., "A Soluble Bone Morphogenetic Protein Extracted from Bone Matrix with a Mixed Aqueous and Nonaqueous Solvent," *Proc. Soc. Exp. Biol. and Med.*, 162, 48–53 (1979).

Urist et al., *Clin. Ortho. Rel. Res.*, 162, 219–232 (1982).

Urist et al., *Proc. Natl. Acad. Sci.*, 76, No. 4, 1828–1832 (1979).

Urist et al., *Proc. Natl. Acad. Sci.*, 81, 371–375 (1984).

Urist et al., *Proc. Soc. Exp. Biol. Med.*, 173, 194–199 (1983).

Urist et al., *Science*, 220, 680–686 (1983).

Urist, *Science*, 150, 893 (1965).

Vieira et al., *Gene*, 19, 259–268 (1982).

Wang et al., *Proc. Natl. Acad. Sci. USA*, 85, pp. 9484–9488, Dec. 1988.

Wang et al., *Proc. Natl. Acad. Sci. USA*, 87, pp. 2220–2224 (1990).

Wozney et al., *Science*, 242, 1528–1534 (1988).

Yeomans et al., *Archs. oral Biol.*, 12, 999–1008 (1967).

Young et al., *Proc. Natl. Acad. Sci. USA*, 80, 1194–1198 (1983).

Purification of Osteogenic Factors

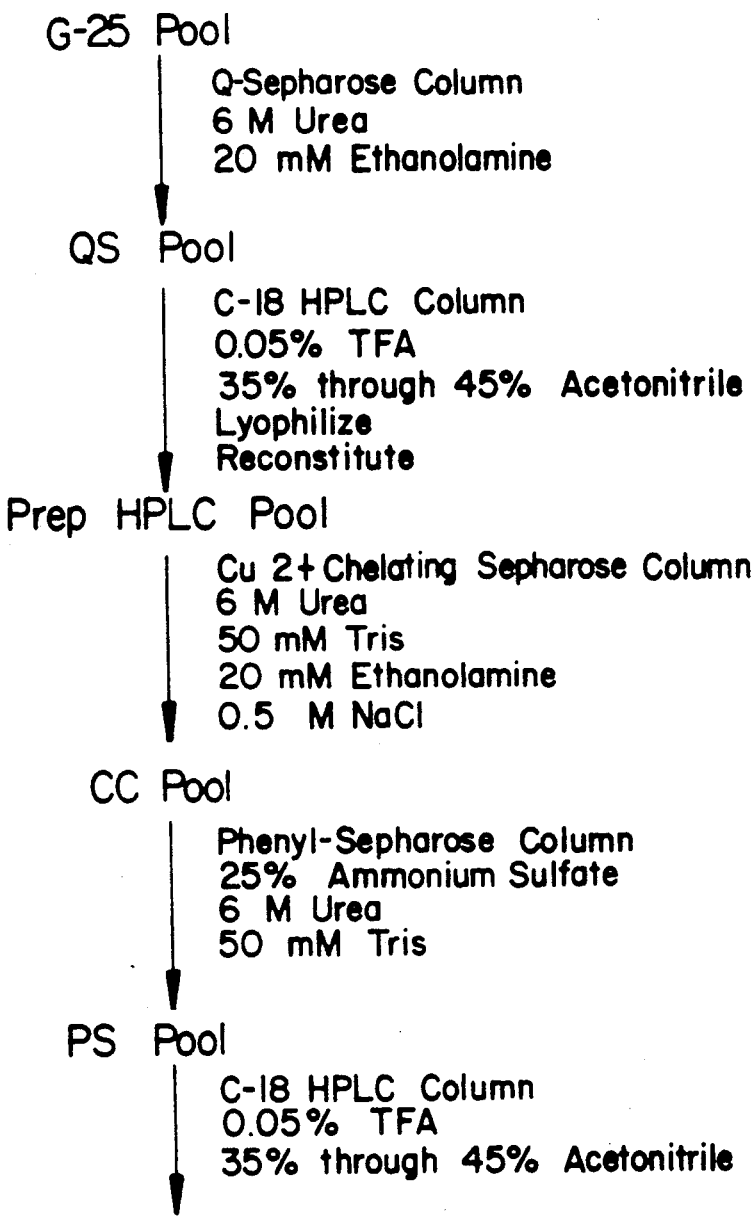
FIG. I cont.

+ DTT

- DTT

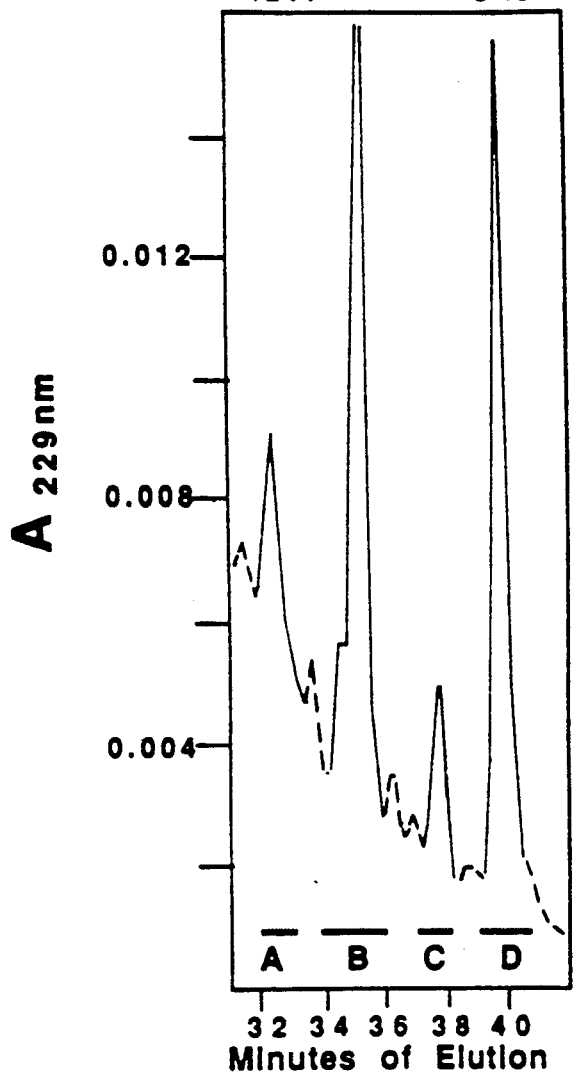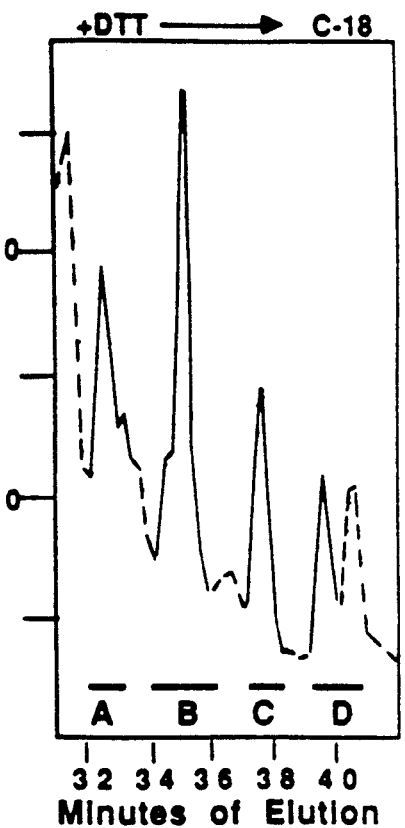
FIG. 5A
FIG. 5B

FIG. 6

```
              10        20        30        40        50        60        70
               |         |         |         |         |         |         |
      TCCACGGGGAGCAAACAGCGCAGCCAGAACCGCTCCAAGACGCCCAAGAACCAGGAAGCCCTGCGGATGGCC

S  T  G  S  K  Q  R  S  Q  N  R  S  K  T  P  K  N  Q  E  A  L  R  M  A 80        90       100       110       120       130       140
               |         |         |         |         |         |         |
      AACGTGGCAGAGAACAGCAGCAGCGACCAGAGGCAGGCCTGTAAGAAGCACGAGCTGTATGTCAGCTTCCGA

N  V  A  E  N  S  S  S  D  Q  R  Q  A  C  K  K  H  E  L  Y  V  S  F  R 150       160       170       180       190       200       210
              |         |         |         |         |         |         |
      GACCTGGGCTGGCAGGACTGGATCATCGCGCCTGAAGGCTACGCCGCCTACTACTGTGAGGGGGAGTGTGCC

D  L  G  W  Q  D  W  I  I  A  P  E  G  Y  A  A  Y  Y  C  E  G  E  C  A 220       230       240       250       260       270       280
              |         |         |         |         |         |         |
      TTCCCTCTGAACTCCTACATGAACGCCACCAACCACGCCATCGTGCAGACGCTGGTCCACTTCATCAACCCG

F  P  L  N  S  Y  M  N  A  T  N  H  A  I  V  Q  T  L  V  H  F  I  N  P 290       300       310       320       330       340       350       360
              |         |         |         |         |         |         |         |
      GAAACGGTGCCCAAGCCCTGCTGTGCGCCCACGCAGCTCAATGCCATCTCCGTCCTCTACTTCGATGACAGC

E  T  V  P  K  P  C. C  A  P  T  Q  L  N  A  I  S  V  L  Y  F  D  D  S 370       380       390       400       410
              |         |         |         |         |
      TCCAACGTCATCCTGAAGAAATACAGAAACATGGTGGTCCGGGCCTGTGGCTGCCAC

```
          10        20        30        40        50        60        70
          |         |         |         |         |         |         |
CAAGCCAAACACAAACAGCGGAAACGCCTTAAGTCCAGCTGTAAGAGACACCCTTTGTACGTGGACTTCAGT
  Q   A   K   H   K   Q   R   K   R   L   K   S   S   C   K   R   H   P   L   Y   V   D   F   S 80        90       100       110       120       130       140
          |         |         |         |         |         |         |
GACGTGGGGTGGAATGACTGGATTGTGGCTCCCCCGGGGTATCACGCCTTTTACTGCCACGGAGAATGCCCT
  D   V   G   W   N   D   W   I   V   A   P   P   G   Y   H   A   F   Y   C   H   G   E   C   P 150       160       170       180       190       200       210
          |         |         |         |         |         |         |
TTTCCTCTGGCTGATCATCTGAACTCCACTAATCATGCCATTGTTCAGACGTTGGTCAACTCTGTTAACTCT
  F   P   L   A   D   H   L   N   S   T   N   H   A   I   V   Q   T   L   V   N   S   V   N   S 220       230       240       250       260       270       280
          |         |         |         |         |         |         |
AAGATTCCTAAGGCATGCTGTGTCCCGACAGAACTCAGTGCTATCTCGATGCTGTACCTTGACGAGAATGAA
  K   I   P   K   A   C   C   V   P   T   E   L   S   A   I   S   M   L   Y   L   D   E   N   E 290       300       310       320       330       340
          |         |         |         |         |         |
AAGGTTGTATTAAAGAACTATCAGGACATGGTTGTGGAGGGTTGTGGGTGTCGC
  K   V   V   L   K   N   Y   Q   D   M   V   V   E   G   C   G   C   R
```

FIG. 8

```
         10        20        30        40        50        60        70
          |         |         |         |         |         |         |
ATGATTCCTGGTAACCGAATGCTGATGGTCGTTTTATTATGCCAAGTCCTGCTAGGAGGCGCGAGCCATGCT

M   I   P   G   N   R   M   L   M   V   V   L   L   C   Q   V   L   L   G   G   A   S   H   A 80        90       100       110       120       130       140
          |         |         |         |         |         |         |
AGTTTGATACCTGAGACGGGGAAGAAAAAAGTCGCCGAGATTCAGGGCCACGCGGGAGGACGCCGCTCAGGG

S   L   I   P   E   T   G   K   K   K   V   A   E   I   Q   G   H   A   G   G   R   R   S   G 150       160       170       180       190       200       210
          |         |         |         |         |         |         |
CAGAGCCATGAGCTCCTGCGGGACTTCGAGGCGACACTTCTGCAGATGTTTGGGCTGCGCCGCCGCCCGCAG

Q   S   H   E   L   L   R   D   F   E   A   T   L   L   Q   M   F   G   L   R   R   R   P   Q 220       230       240       250       260       270       280
          |         |         |         |         |         |         |
CCTAGCAAGAGTGCCGTCATTCCGGACTACATGCGGGATCTTTACCGGCTTCAGTCTGGGGAGGAGGAGGAA

P   S   K   S   A   V   I   P   D   Y   M   R   D   L   Y   R   L   Q   S   G   E   E   E   E 290       300       310       320       330       340       350       360
          |         |         |         |         |         |         |         |
GAGCAGATCCACAGCACTGGTCTTGAGTATCCTGAGCGCCCGGCCAGCCGGGCCAACACCGTGAGGAGCTTC

E   Q   I   H   S   T   G   L   E   Y   P   E   R   P   A   S   R   A   N   T   V   R   S   F 370       380       390       400       410       420       430
                   |         |         |         |         |         |         |
CACCACGAAGAACATCTGGAGAACATCCCAGGGACCAGTGAAAACTCTGCTTTTCGTTTCCTCTTTAACCTC

H   H   E   E   H   L   E   N   I   P   G   T   S   E   N   S   A   F   R   F   L   F   N   L 440       450       460       470       480       490       500
                  |         |         |         |         |         |         |
AGCAGCATCCCTGAGAACGAGGCGATCTCCTCTGCAGAGCTTCGGCTCTTCCGGGAGCAGGTGGACCAGGGC

```
        510       520       530       540       550       560       570
         |         |         |         |         |         |         |
CCTGATTGGGAAAGGGGCTTCCACCGTATAAACATTTATGAGGTTATGAAGCCCCCAGCAGAAGTGGTGCCT
  P  D  W  E  R  G  F  H  R  I  N  I  Y  E  V  M  K  P  P  A  E  V  V  P 580       590       600       610       620       630       640
         |         |         |         |         |         |         |
GGGCACCTCATCACACGACTACTGGACACGAGACTGGTCCACCACAATGTGACACGGTGGGAAACTTTTGAT
  G  H  L  I  T  R  L  L  D  T  R  L  V  H  H  N  V  T  R  W  E  T  F  D 650       660       670       680       690       700       710       720
    |         |         |         |         |         |         |         |
GTGAGCCCTGCGGTCCTTCGCTGGACCCGGGAGAAGCAGCCAAACTATGGGCTAGCCATTGAGGTGACTCAC
  V  S  P  A  V  L  R  W  T  R  E  K  Q  P  N  Y  G  L  A  I  E  V  T  H 730       740       750       760       770       780       790
         |         |         |         |         |         |         |
CTCCATCAGACTCGGACCCACCAGGGCCAGCATGTCAGGATTAGCCGATCGTTACCTCAAGGGAGTGGGAAT
  L  H  Q  T  R  T  H  Q  G  Q  H  V  R  I  S  R  S  L  P  Q  G  S  G  N 800       810       820       830       840       850       860
         |         |         |         |         |         |         |
TGGGCCCAGCTCCGGCCCCTCCTGGTCACCTTTGGCCATGATGGCCGGGGCCATGCCTTGACCCGACGCCGG
  W  A  Q  L  R  P  L  L  V  T  F  G  H  D  G  R  G  H  A  L  T  R  R  R 870       880       890       900       910       920       930
         |         |         |         |         |         |         |
AGGGCCAAGCGTAGCCCTAAGCATCACTCACAGCGGGCCAGGAAGAAGAATAAGAACTGCCGGCGCCACTCG
  R  A  K  R  S  P  K  H  H  S  Q  R  A  R  K  K  N  K  N  C  R  R  H  S
            ↑

940       950       960       970       980       990       1000
         |         |         |         |         |         |         |
CTCTATGTGGACTTCAGCGATGTGGGCTGGAATGACTGGATTGTGGCCCCACCAGGCTACCAGGCCTTCTAC
  L  Y  V  D  F  S  D  V  G  W  N  D  W  I  V  A  P  P  G  Y  Q  A  F  Y
```

FIG. 8 CONT.'

```
    1010      1020      1030      1040      1050      1060      1070      1080
     |         |         |         |         |         |         |         |
TGCCATGGGGACTGCCCCTTTCCACTGGCTGACCACCTCAACTCAACCAACCATGCCATTGTGCAGACCCTG

C  H  G  D  C  P  F  P  L  A  D  H  L  N  S  T  N  H  A  I  V  Q  T  L 1090      1100      1110      1120      1130      1140      1150
     |         |         |         |         |         |         |
GTCAATTCTGTCAATTCCAGTATCCCCAAAGCCTGTTGTGTGCCCACTGAACTGAGTGCCATCTCCATGCTG

V  N  S  V  N  S  S  I  P  K  A  C  C  V  P  T  E  L  S  A  I  S  M  L 1160      1170      1180      1190      1200      1210      1220
     |         |         |         |         |         |         |
TACCTGGATGAGTATGATAAGGTGGTACTGAAAAATTATCAGGAGATGGTAGTAGAGGGATGTGGGTGCCGC

Y  L  D  E  Y  D  K  V  V  L  K  N  Y  Q  E  M  V  V  E  G  C  G  C  R
```

HETERODIMERIC OSTEOGENIC FACTOR

BACKGROUND OF THE INVENTION

This is a continuation-in-part of application Ser. No. 07/415,555 filed Oct. 4, 1989 which issued Apr. 21, 1992 as U.S. Pat. No. 5,106,626 and which is a continuation-in-part of application Ser. No. 07/256,034 filed Oct. 11, 1988, now abandoned.

The present invention relates to novel preparations of osteogenic factors, methods for their isolation and uses thereof (to repair bone defects). The preparations so isolated exhibit the ability to promote or stimulate the formation of bone at the site of their application. Bone is a highly specialized connective tissue with unique mechanical properties derived from its extensive matrix structure. A network of fibrous bundles composed of the protein, collagen, is presumed to provide the tension-resistant behavior of bone. In addition, other materials including proteoglycans, noncollagenous proteins, lipids and acidic proteins associated with a mineral phase consisting primarily of poorly crystallized hydroxyapatite are deposited in the extensive matrix architecture of bone. Bone tissue is continuously renewed, by a process referred to as remodeling, throughout the life of mammals. This physiologic process might serve to maintain the properties of a young tissue.

The processes of bone formation and renewal are carried out by specialized cells. Osteogenesis vis-a-vis morphogenesis and growth of bone is presumably carried out by the "osteoblasts" (bone-forming cells). Remodeling of bone is apparently brought about by an interplay between the activities of the bone-resorbing cells called "osteoclasts" and the bone-forming osteoblasts. The bony skeleton is thus not only an architectural structure with a mechanical function but also is a living tissue capable of growth, modeling, remodeling and repair. Since these processes are carried out by specialized living cells, chemical (pharmaceutical/hormonal), physical and physicochemical alterations can affect the quality, quantity and shaping of bone tissue.

A variety of pathological disorders as well as physical stress (for example, fracture) necessitate active formation of bone tissue at rates that are significantly higher than that which can be supported by the normal milieu of the body. It is thus of value to identify physiologically acceptable substances (hormones/pharmaceuticals/growth factors) that can induce the formation of bone at a predetermined site where such substances are applied, for example, by implantation. Such agents could either provide a permissive matrix structure for the deposition of bone-forming cells, or stimulate bone-forming cells, or induce the differentiation of appropriate progenitors of bone-forming cells.

The presence of proteinaceous and prostaglandin-like growth stimulators for osteoblasts has been examined, see reviews: Raisz, et al., *New Engl. J. Med.*, 309(1), 29–35 (1983) and Raisz, et al., *New Engl. J. Med.*. 309(2), 83–89 (1983).

The observation that a bone graft from the same individual or a compatible individual leads to the formation of new healthy bone at the site of the graft, led to the hypothesis that bone contains active proteins which promote local osteogenesis. Urist, et al. disclosed evidence that bone matrix-associated noncollagenous proteins can be isolated by dissociative treatment of demineralized bone powder and that this mixture of noncollagenous proteins contain the local osteoinductive capability which was designated by Urist (e.g., *Science.* 150, 893 (1965)) as bone morphogenetic activity.

A variety of osteogenic, cartilage-inducing and bone-inducing protein preparations have been described in the art. Urist, et al. and others have described various partially fractionated protein preparations with osteoinductive properties. These preparations are fractionated from the noncollagenous protein mixture extracted using different dissociative treatment of demineralized bone powder and subjecting the extract to various protein fractionation steps. Several such preparations have been characterized by different assays to determine their biological activities and by protein components identified using different standard protein analytical methods.

Urist, et al., *Proc. Natl. Acad. Sci. (USA)*, 81, 371–375 (1984), discloses that bovine BMP has an apparent molecular Weight of 18.5K daltons. The publication further discloses other bone derived proteins with apparent molecular weights of 17.5K and 17K, proteins with higher molecular weights of 34K, 24K and 22K and a protein with a lower molecular weight of 14K. The publication provided the N-terminal sequence for the 17.5K protein which had an unblocked amino terminus.

Urist, European Patent Application No. 212,474, discloses peptide fragments having molecular weights between about 4K and 7K comprising at least an active portion of the osteoinductive and immunoreactive domain of the 17.5K BMP molecule.

Wang, et al., Patent Cooperation Treaty Application No. WO 88/00205, discloses a bovine bone inductive factor which is isolated from demineralized bone powder by a procedure comprising a number of chromatographic and dialysis steps. The bone inductive factor so isolated was found to contain, as judged by a non-reducing SDS-PAGE analysis, one or more proteins having a molecular weight of approximately 28,000 to 30,000 daltons. Reducing SDS-PAGE analysis of the active protein(s) yielded two major bands having the mobility of proteins having molecular weights of 18,000 daltons and 20,000 daltons respectively. Wang, et al., discloses three bovine proteins designated BMP-1, BMP-2 and BMP-3 where BMP is bone morphogenetic protein and provides peptide sequences for the proteins. Wang, et al., also discloses the nucleotide sequences and amino acid sequences predicted thereby of four human proteins designated BMP-1, BMP-2 Class I, BMP-2 Class II and BMP-3.

Wozney, et al., *Science,* 242, 1528–1533 (1988), describes the nucleotide sequences and amino acid sequences predicted thereby of three human complementary DNA clones (designated BMP-1, BMP-2A and BMP-3) corresponding to three polypeptides present in an extract of bovine bone which is capable of inducing de novo bone formation. Recombinant human BMP-1, BMP-2A and BMP-3 proteins were said to be independently capable of inducing the formation of cartilage in vivo. The nucleotide sequence and derived amino acid sequence of a fourth complementary DNA clone (designated BMP-2B) is also described. The BMP-1, BMP-2A, BMP-2B and BMP-3 proteins of this publication appear to correspond, respectively, to the BMP-1, BMP-2 Class I, BMP-2 Class II and BMP-3 proteins.

Kubersampath, et al., Patent Cooperation Treaty Application No. WO 89/09787 claiming priority based on applications including U.S. patent application Ser. No. 179,406 filed Apr. 8, 1988 and Oppermann, et al., Patent Cooperation Treaty Application No. WO 89/09788 claiming priority based on applications including U.S. patent application Ser. No. 179,406 filed Apr. 8, 1988 disclose nucleotide sequences and amino acid sequences predicted thereby of a human protein designated OP-1 and certain consensus nucleotide sequences and their amino acid sequences predicted thereby. These recombinant proteins are said to be independently capable of inducing the formation of bone in vivo.

Wang, et al., *Proc. Natl. Acad. Sci. USA*, 87, pp. 2220-2224 (1990), describe the nucleotide sequence and amino acid sequence predicted thereby of a human protein designated BMP-2A, corresponding to a polypeptide present in an extract of bovine bone which is capable of inducing de novo bone formation. Recombinant human BMP-2A protein is said to be independently capable of inducing the formation of bone in vivo.

Kubersampath, et al., *J. Biol. Chem.*, 265, 13198-13205 (1990), describes a bovine bone-derived protein that induces bone formation. The bone-inductive protein was found to contain, as judged by a non-reducing SDS-PAGE analysis, a protein with a molecular weight of approximately 30,000 daltons. Reducing SDS-PAGE analysis yielded two major bands corresponding to molecular weights of 18,000 and 16,000 daltons. The 18,000-dalton subunit is the protein product of the bovine equivalent of the human OP-1 gene and the 16,000-dalton subunit is the protein product of the bovine equivalent of the human BMP-2A gene.

Celeste, et al., *Proc. Natl. Acad. Sci. USA*. 87, 9843-9847 (1990), describe the human protein sequences derived from the nucleotide sequence of six genes encoding proteins related to TGF-$\beta$. These encoded proteins are designated BMP-2, BMP-3, BMP-4, BMP-5, BMP-6 and BMP-7.

SUMMARY OF THE INVENTION

The present invention is directed to novel preparations of osteogenic factors, methods for their isolation and uses thereof. Specifically, the invention is based on the discovery that a primary osteogenically active protein of P3 OF 31-34 is a heterodimer of P3 OF 31-34 subunit B (hereinafter "subunit B") and P3 OF 31-34 subunit D (hereinafter "subunit D"). Preparations comprising the B/D heterodimer are characterized by the ability to stimulate osteogenesis. The invention provides a method of producing an osteogenic protein preparation comprising a heterodimer of a first polypeptide subunit and a second polypeptide subunit comprising the steps of culturing in a suitable culture media one or more cell lines transformed with a first and a second nucleotide sequence, said first nucleotide sequence being selected from the group consisting of: the nucleotide sequence encoding subunit B as shown in SEQ ID NO: 3; a nucleotide sequence which encodes the same sequence of amino acids as encoded by the nucleotide sequence shown in SEQ ID NO: 3; a nucleotide sequence which is at least 80% homologous with the nucleotide sequence shown in SEQ ID NO: 3 and which encodes a homologue of subunit B having the osteogenic activity of P3 OF 31-34 subunit B; and a nucleotide sequence which would be at least 80% homologous with the nucleotide sequence shown in SEQ ID NO: 3 but for the redundancy of the genetic code and which encodes a homologue of subunit B having the osteogenic activity of p3 OF 31-34 subunit B. The second nucleotide sequence is selected from the group consisting of: the nucleotide sequence encoding subunit D as shown in SEQ ID NO: 1; a nucleotide sequence which encodes the same sequence of amino acids as encoded by the nucleotide sequence shown in SEQ ID NO: 1; a nucleotide sequence which is at least 80% homologous with the nucleotide sequence shown in SEQ ID NO: 1 and which encodes a homologue of subunit D having the osteogenic activity of P3 OF 31-34 subunit D; and a nucleotide sequence which would be at least 80% homologous with the nucleotide sequence shown in SEQ ID NO: 1 but for the redundancy of the genetic code and which encodes a homologue of subunit D having the osteogenic activity of P3 OF 31-34 subunit D. The cell line(s) is (are) cultured to produce the first and second polypeptide subunits which are linked with a disulfide bond to form heterodimers and are isolated. The B/D heterodimers are preferably purified and isolated according to the steps of subjecting the culture medium to a series of chromatography steps utilizing a Q-Sepharose column, an S-Sepharose column and a Phenyl-Sepharose column to recover an active fraction. The active fraction is then subjected to reverse phase chromatography using a C-18 high performance liquid chromatography column equilibrated with buffers containing trifluoroacetic acid and acetonitrile by eluting the active preparation at concentrations between 35% and 45% acetonitrile. The invention further provides the osteogenic preparations prepared thereby and pharmaceutical products comprising the osteogenic preparation so made. Also provided by the invention is a method for transforming a cell with genes encoding both subunits B and D and homologues thereof and cells transformed thereby. The invention further provides vectors comprising a first and a second DNA sequence in operative association with an expression control sequence which sequence encode subunits B and D or homologies thereof. In addition, the invention provides a method for inducing bone formation in a mammal comprising administering to the mammal an effective amount of the osteogenic preparation comprising heterodimers of subunits B and D or homologues thereof. The invention further provides compositions for implantation into a mammal comprising the osteogenic preparation comprising heterodimers of subunits B and D admixed with a physiologically acceptable matrix material.

BRIEF DESCRIPTION OF THE FIGURES

FIG. 5A shows the isolation and identification of subunits of the P3 OF 31-34 proteins eluting in fraction 26, from the reverse phase HPLC of the PS Pool.

FIG. 5B shows the isolation and identification of subunits of the P3 OF 31-34 proteins eluting in fraction 28 from the reverse phase HPLC of the PS Pool.

FIG. 6 shows the nucleotide and derived amino acid sequences, also set out in SEQ ID NOS: and 2, of the cDNA gene for human mature D.

FIG. 7 shows the nucleotide and derived amino acid sequences, also set out in SEQ ID NOS: 3 and 4, of the cDNA gene for human mature B.

FIG. 8 shows the nucleotide and derived amino acid sequences, also set out in SEQ ID NOS: 5 and 6, of the cDNA gene for human C.

DETAILED DESCRIPTION OF THE INVENTION

Figure 1:
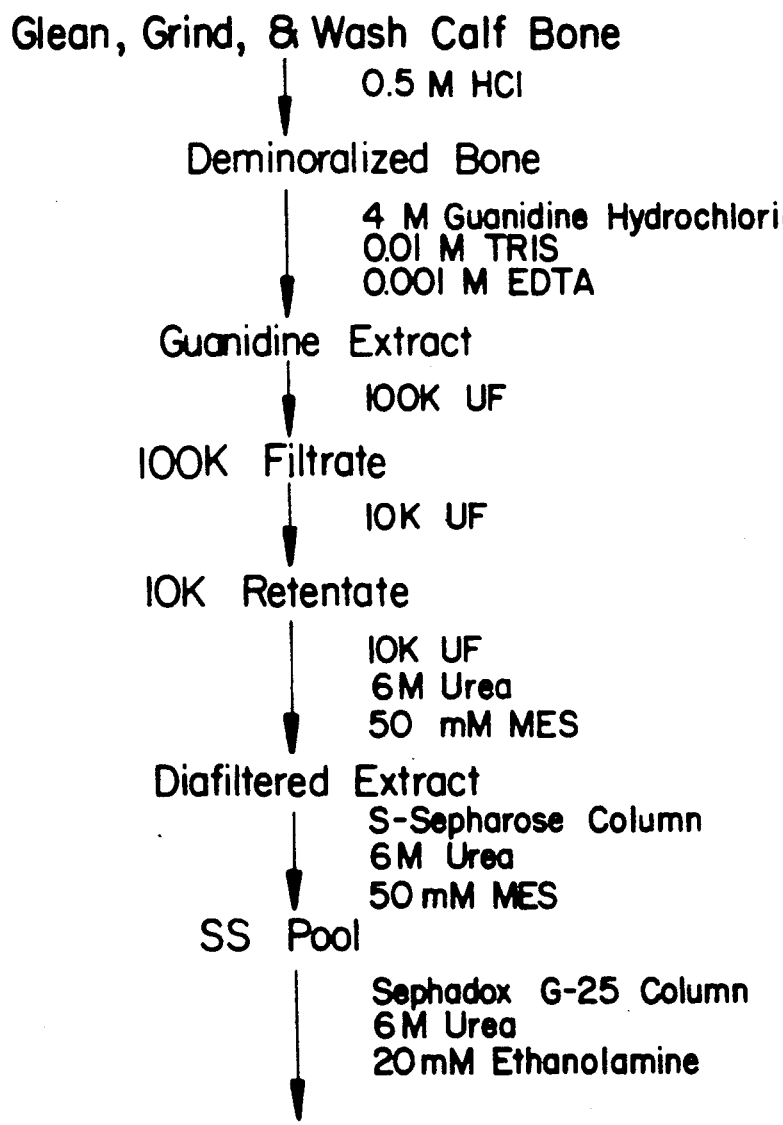
FIG. 1 illustrates a method for the purification of P3 OF 31-34 (osteogenic factors) proteins from calf bone.

The present invention relates to the osteogenic preparation known as P3 OF 31-34 which has previously been characterized by applicants as comprising osteogenically active proteins which during gel filtration during non-reducing and dissociative conditions, elute as proteins having apparent molecular weights within the range of about 31,000 to 34,000 daltons. In co-owned and copending U.S. patent application Ser. No. 07/415,555 filed Oct. 4, 1989 the disclosure of which is hereby incorporated by reference it is disclosed that the P3 OF 31-34 osteogenic protein material yields four distinct peaks when analyzed by reverse phase HPLC after reduction. When analyzed by reducing SDS-PAGE and silver staining, three of the peaks are characterized as protein subunits migrating with apparent molecular weights within the range of 17,500 to 19,000 daltons, and the fourth peak is characterized as a protein subunit migrating with an apparent molecular weight within the range of 16,000 to 17,500 daltons. The polypeptide subunits of P3 OF 31-34 have been designated as subunits A, B, C and D. The subunits have been characterized by amino acid sequences and cDNA sequences encoding the subunits. The present invention is based on the discovery that a primary osteogenically active protein comprises a heterodimer of P3 OF 31-34 subunit B and P3 OF 31-34 subunit D wherein the subunits are linked by at least one disulfide bond.

The osteogenic protein preparation comprising the B/D heterodimer may be used to form a composition for implantation into a mammal by admixture with a physiologically acceptable matrix material. In addition, devices for implantation into mammals comprising a structural member encoated with the osteogenic factor/matrix composition are provided by the invention.

The present invention is intended to encompass osteogenically active heterodimers of subunit B and D analogues. Specifically, it is contemplated that various deletions, insertions and substitutions can be made in the amino acid sequences of subunits B and D such that the sequences will vary from those which are present in naturally derived mammalian B/D heterodimer. The B/D heterodimer and its subunits can also be chemically or enzymatically modified, can be fusion proteins or can be bound to suitable carrier substances such as a polymer. To the extent that such molecules retain osteogenic activity, they are contemplated as being within the scope of the present invention.

The subunit B and D polypeptides can be produced by expression of DNA prepared by molecular cloning technologies or by chemical synthesis of oligonucleotide and assembly of the oligonucleotide by any of a number of techniques prior to expression in a host cell. [See, e.g., Caruthers, U.S. Pat. No. 4,500,707; Balland, et al., Biochimie, 67, 725-736 (1985); Edge, et al., Nature, 292, 756-762 (1981)]. Messenger RNA encoding subunits B or D or analogs thereof may also be expressed in vitro. Changes in activity levels are measured by the appropriate assay. Modifications of such protein properties as redox or thermal stability, hydrophobicity, susceptibility to proteolytic degradation, or the tendency to aggregate with carriers or into multimers are assayed by methods well known to those of ordinary skill in the art.

Prokaryotic microorganisms (such as bacteria) and eukaryotic microorganisms (such as yeast) may be employed as host cells according to the present invention. S. cerevisiae, or common baker's yeast, is the most commonly used among eukaryotic microorganisms, although a number of other strains are commonly available. For expression in bacteria and yeast, cloning and expression vectors are well known to those skilled in the art, such as lambda phage and pBR322 in E. coli and YRp7 in S. cerevisiae.

Cells derived from multicellular eukaryotes may also be used as hosts. Cells from vertebrate or invertebrate eukaryotes may be used, and those skilled in the art know of appropriate expression vectors for use therein, such as SV40 retroviral and papilloma viral vectors for mammalian host cells, NPV vectors for invertebrate host cells and Ti vectors for plant cells.

It is preferred that host cells be transformed with genes encoding both subunits B and D in order that intracellular processing link the subunits with at least one disulfide bond. Nevertheless, it is contemplated that the subunits can be separately expressed and the subunits be dimerized in vitro utilizing denaturation/renaturation techniques known in the art.

The present invention further discloses methods of using the B/D heterodimers and compositions which comprise them as pharmaceutical agents for the stimulation of bone growth in mammals. Pharmaceutically acceptable compositions comprised of one or more of the proteins and/or active polypeptides and/or immunologically related entities in combination with a pharmaceutically acceptable carrier are also disclosed herein. Such compositions can optionally contain other bioactive materials or other ingredients which aid in the administration of the composition or add to the effectiveness of the composition.

The term "osteogenesis" means formation of new bone or induction of growth of pre-existing bones at specific sites in response to local administration (for example, implantation of an active preparation in a pharmaceutically acceptable manner). The term "osteogenic amount" refers to an amount of the osteogenic protein and/or active polypeptide and/or immunologically related entity sufficient to provide the desired effect. The term "osteogenically active" or "osteogenic" means that the preparation has the capability to promote or induce osteogenesis.

The application of the osteogenic factors can be conveniently accomplished by administering, such as by implanting, a lyophilized preparation or suspension of one or more of the osteogenic proteins and/or one or more active polypeptide and/or one or more immunologically related entities in sufficient quantity to promote osteogenesis at the desired site. Alternatively, pharmaceutically acceptable compositions can be used which are comprised of one or more of the osteogenic proteins and/or one or more of the active polypeptides and/or one or more of the immunologically related entities described herein and a pharmaceutically acceptable matrix such as collagenous proteins or matrix material derived from powdered bone extracted with strong denaturing agents, or other pharmaceutically acceptable carriers.

While the B/D heterodimer is a major osteogenically active protein, it is contemplated that preparations comprising the B/D heterodimer in combination with other homo- and heterodimers of P3 OF 31-34 subunits A, B, C, D and E may provide synergistic effects with respect to osteogenic activity.

The following examples are included to further illustrate the invention but are not to be construed as limitations thereon.

EXAMPLE 1

Purification of Bovine Osteogenic Factors

According to this example, bovine osteogenic factors were isolated from demineralized calf bone powder according to the procedure disclosed in FIG. 1. Approximately 200 pounds of diaphysial sections of calf bone were scraped clean of connective tissue and marrow was removed. The demarrowed sections were ground to a powder and washed with approximately 2100 liters of cold deionized water. The bone powder was allowed to settle during the water washes and the suspended connective tissue fragments were removed with the supernatant and discarded.

The bone powder was suspended in a total of approximately 570 liters of cold 0.5 M HCl for about 2 hours and was then allowed to settle. The HCl was removed with the supernatant and discarded. The remaining HCl was removed by washing the bone powder with approximately 700 liters of cold deionized water, followed by approximately 350 liters of cold 0.1 M Tris, pH 7, solution. The demineralized bone powder (demineralized bone) was allowed to settle and the supernatant was discarded.

The demineralized bone powder was suspended in approximately 140 liters of cold 4 M guanidine hydrochloride containing 0.01 M Tris, pH 7, and 0.001 M EDTA for about 20 hours. The extracted bone powder was removed by filtration and discarded. The supernatant (guanidine extract) was saved.

The guanidine extract was filtered through Amicon hollow fiber cartridges (H10-P100-20) with an average molecular weight cutoff of 100,000 daltons. The 100,000 dalton filtrate (100K filtrate) was then concentrated through Amicon spiral cartridges (S10Y10) with molecular weight cutoffs of 10,000 daltons. The 10,000 dalton retentate (10K retentate) was saved and assayed for pH, conductivity, total protein content by BCA colorimetric protein assay (Pierce Chemicals, Rockford, Ill.), resolution of protein constituents in the preparations using reducing SDS-PAGE followed by silver staining or Coomassie Blue staining and determination of the osteogenic activity using the rat implant assay disclosed below in Example 2.

The 10K retentate was exchanged into 6 M urea containing 50 mM 2-(N-morpholino)ethanesulfonic acid (MES), pH 6.5, by diafiltration with an Amicon spiral cartridge (S10Y10) with a molecular weight cutoff of 10,000 daltons.

The diafiltered extract was adjusted to a pH of 6.5 using 5 M NaOH and a conductivity of 10 mS/cm using 5 M NaCl and applied to a 0.4 liter S-Sepharose column (Pharmacia Chemicals, New Jersey) equilibrated with 6 M urea containing 50 mM MES, pH 6.5, adjusted to conductivity of 10 mS/cm. The column was washed with 2.4 liters of 6.0 M urea containing 50 mM MES, pH 6.5, adjusted to a conductivity of 10 mS/cm to elute the unbound proteins. The S-Sepharose active pool (SS Pool) was eluted with 1.2 liters of 6.0 M urea containing 50 mM MES, pH 6.5, and 0.5 M NaCl. The S-Sepharose active pool was concentrated using membrane filters with an average molecular weight cutoff of 10,000 daltons. The pH and conductivity of the preparation were determined, the total protein content was measured by BCA protein assay, the protein constituents were analyzed using SDS-PAGE followed by silver staining and the osteogenic activity was determined using the rat implant assay.

The S-Sepharose active pool was exchanged into 6 M urea containing 20 mM ethanolamine, pH 9.5 by diafiltration with an Amicon spiral cartridge (S10Y10) with a molecular weight cutoff of 10,000 daltons.

The G-25 Pool was applied to a 0.7 liter Q-Sepharose column (Pharmacia Chemicals, New Jersey) equilibrated with 6 M urea containing 20 mM ethanolamine, pH 9.5. The column was washed with 2.1 liters of 6 M urea containing 20 mM ethanolamine, pH 9.5, to elute the unbound proteins. The osteogenically active protein pool (QS Pool) was eluted from Q-Sepharose column with 1.4 liters of 6 M urea containing 20 mM ethanolamine, pH 9.5, and 0.2 M NaCl. The QS Pool was adjusted to a pH of 6-7 with glacial acetic acid and concentrated using membrane filters with an approximate molecular weight cutoff of 10,000 daltons. The QS Pool was assayed for pH and conductivity; the total protein content was determined by BCA protein assay, the protein constituents were analyzed by reducing SDS-PAGE followed by silver staining and the osteogenic activity was measured using the rat implant assay.

The QS Pool was then applied to a preparative C-18 HPLC column equilibrated with a buffer containing, by volume, 70% Buffer A (Buffer A is 0.05% trifluoroacetic acid in water) and 30% Buffer B (Buffer B is 0.025% trifluoroacetic acid in acetonitrile). Bound proteins were eluted using a linear gradient of 30% to 60% acetonitrile in 120 minutes. The osteogenic activity (Prep HPLC Pool) eluted within the concentrations of 35% to 45% acetonitrile. The Prep HPLC Pool was lyophilized and resuspended in 1 ml of water. The Prep HPLC Pool was assayed for pH and conductivity; the total protein content was determined by BCA protein assay, the protein constituents were analyzed by reducing SDS-PAGE followed by silver staining and the osteogenic activity was measured using the rat implant assay.

The Prep HPLC Pool was adjusted to a protein concentration of 0.5 mg/ml in 6 M urea containing 50 mM Tris, pH 7.5-8.0, 20 mM ethanolamine and 0.5 M NaCl and was applied to a 5-10 ml Chelating-Sepharose 6B column (Pharmacia Chemicals, New Jersey) charged with $Cu^{2+}$ and equilibrated with 6 M urea containing 50 mM Tris, pH 7.5-8.0, 20 mM ethanolamine and 0.5 M NaCl. The column was washed with 5 column volumes of equilibration buffer followed by 10 column volumes of 6 M urea containing 50 mM Tris, pH 7.4-7.8, to elute the unbound proteins. Bound proteins were eluted with 10 column volumes of 6 M urea containing 50 mM Tris, pH 7.4-7.8, and 4 mM imidazole. The osteogenic activity (CC Pool) was eluted from the copper chelate column with 10 column volumes of 6 M urea containing 50 mM Tris, pH 7.4-7.8, and 15 mM imidazole. The CC Pool was assayed for total protein as estimated by absorbance at 280 nm, and its osteogenic activity was measured using the rat implant assay.

The CC Pool was adjusted to 25% ammonium sulfate and loaded onto a 1-3 ml column of Phenyl-Sepharose (Pharmacia Chemicals, New Jersey) equilibrated with 6 M urea containing 25% ammonium sulfate, 50 mM Tris pH 7.4-7.8. The column was washed with 10 column volumes of 6 M urea containing 25% ammonium sulfate, and 50 mM Tris pH 7.4-7.8, to elute the unbound proteins. Bound proteins were eluted with 10 column volumes of 6 M urea containing 15% ammonium sulfate, 50 mM Tris pH 7.4-7.8. The osteogenic activity (PS Pool) was eluted from the Phenyl-Sepharose column with 6 M urea containing 50 mM Tris pH 7.4-7.8, was assayed for total protein as estimated by absorbance at 280 nm, and its osteogenic activity was measured using the rat implant assay.

The PS Pool was applied to a semi-preparative or analytical C-18 HPLC column equilibrated with a buffer containing, by volume, 70% Buffer A and 30% Buffer B (Buffer A is 0.05% trifluoroacetic acid in water and Buffer B is 0.025% trifluoroacetic acid in acetonitrile). Bound proteins were eluted using a linear gradient of 30% to 60% acetonitrile. As was previously characterized, the osteogenic activity (HPLC Pool) eluted within the concentrations of 35% to 45% acetonitrile. The HPLC Pool was assayed for total protein as estimated by absorbance at 229 nm and its osteogenic activity was measured using the rat implant assay.

EXAMPLE 2

Biological Activity

The induction of bone matrix was measured using a rat implant assay as generally described by Sen, Walker and Einarson (1986), in Development and Diseases of Cartilage and Bone Matrix, eds. A. Sen and T. Thornhill, 201-220, Alan R. Liss, New York; and Sampath, et al., Proc. Natl. Acad. Sci. (USA), 80, 6591-6595 (1983). Approximately 70-100 mg of inactive bone matrix (bone collagen) was mixed with an aqueous solution of osteogenic protein preparation and the water removed by lyophilization. The dried coated granules were packed in gelatin capsules (Eli Lilly #5) and each capsule was subcutaneously implanted near the thigh muscles in each back leg of male Long Evans rats. The implanted rats were sacrificed 17 to 28 days following implantation and the implant tissue was surgically removed and placed in Bouin's Solution. The specimens were then decalcified and processed for toluidine blue stained sections. Histomorphology and percent ossification was determined by examination of the stained sections. Potency is defined by the amount of protein (mg) required for implantation with inactive bone matrix yielding at least 10% of the area of the stained sections occupied by osteoid activity.

TABLE 1

PURIFICATION OF OSTEOGENIC FACTORS

| Sample | Total Protein | Potency in Rat (mg/implant) |
|---|---|---|
| Guanidine Extract | 130,000-170,000 mg | |
| 10K Retentate | 6,000-15,000 mg | 10.0 |
| S-S Pool | 300-900 mg | 1.0 |
| QS Pool | 70-250 mg | 0.25 |
| Prep HPLC Pool | 4-12 mg | 0.05 |
| CC Pool | 2-5 mg | 0.025 |
| PS Pool | 0.5-1 mg | 0.01 |
| HPLC Pool | 0.01-0.05 mg | 0.001 |

The increase in potency of the various osteogenically active protein preparations obtained using purification steps according to Example 1 is shown in Table 1, above, with the HPLC Pool having a potency of 0.001 mg/implant.

EXAMPLE 3

Figure 2B:
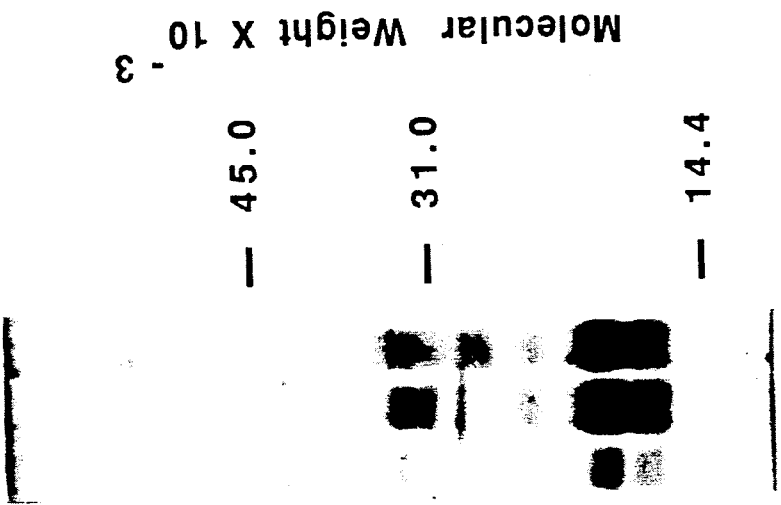
FIG. 2B shows reducing SDS polyacrylamide gel electrophoresis of P3 OF 31-34 proteins followed by silver staining.
Figure 2A:
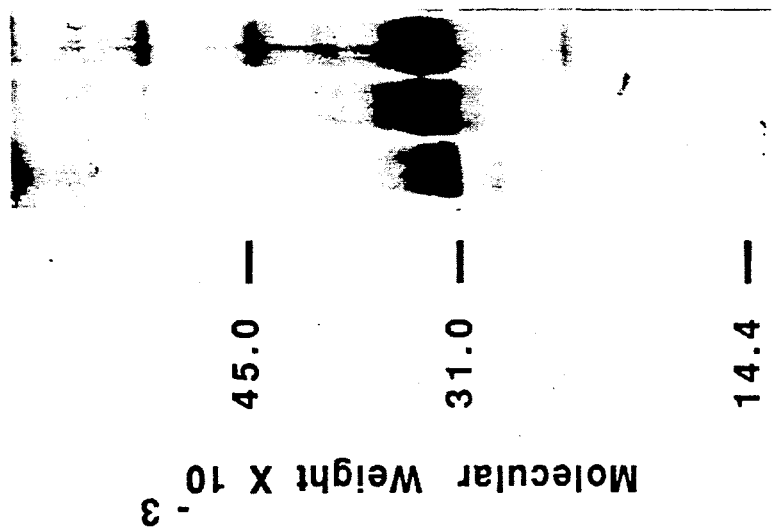
FIG. 2A shows the apparent molecular weight of the osteogenic factors as determined by non-reducing SDS polyacrylamide gel electrophoresis followed by silver staining.

Determination of Molecular Weights of Purified Osteogenic Factors Under Reducing and Nonreducing Conditions and Purification of Reduced Subunits Purified osteogenically active protein preparation as obtained in the HPLC Pool of Example 1 were suspended in SDS dilution buffer in the absence of reducing reagents (−DTT), electrophoresed on 12.5% or 15% SDS polyacrylamide gels and the protein bands visualized by silver staining. Molecular weights are determined relative to non-prestained molecular weight standards (Bio-Rad). This gel system revealed that the HPLC Pool contained protein bands which migrate within the molecular weight range of 31,000-34,000 daltons (see FIG. 2A).

Purified osteogenically active proteins in the HPLC Pool were subjected to an alternative analytical method whereby protein subunits held together by disulfide bonds can be resolved by reduction of these bonds in SDS dilution buffer in the presence of a reducing agent (dithiothreitol or beta-mecaptoethanol) and electrophoresis on 12.5% or 15% SDS polyacrylamide gels. Molecular weights were determined relative to non-prestained molecular weight standards (Bio-Rad). In this gel system, the HPLC Pool revealed proteins migrating as two broad bands within the molecular weight ranges of 16,000-17,500 and 17,500-19,000 daltons (see FIG. 2B).

Figure 3A:
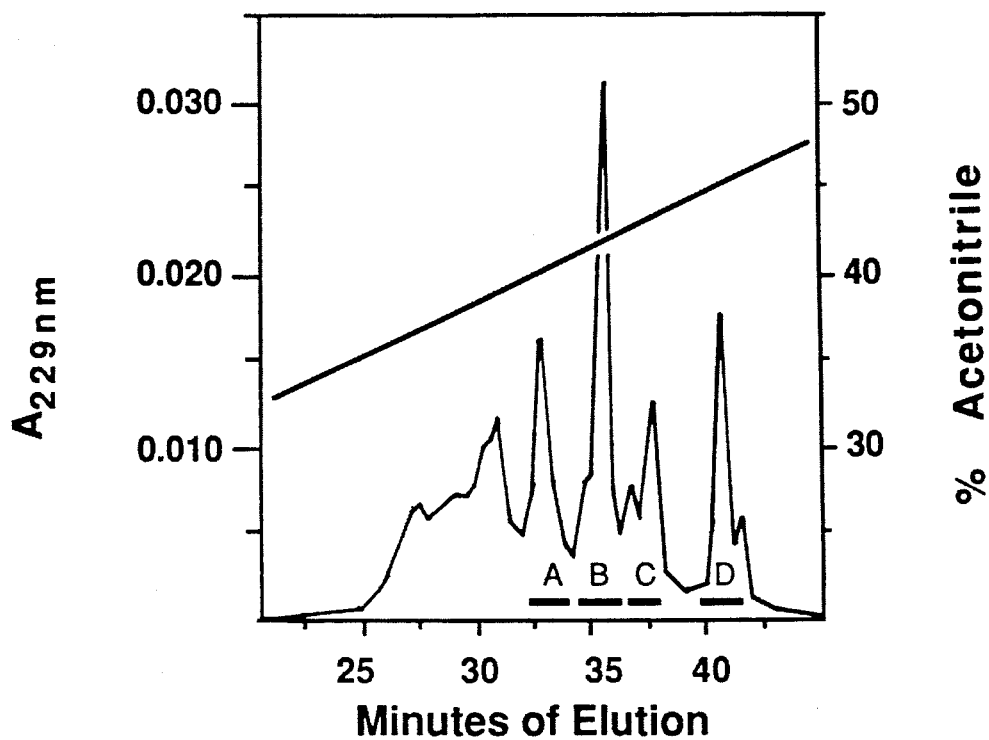
FIG. 3A shows the isolation of the subunits of the P3 OF 31-34 proteins (osteogenic factors) by reverse phase HPLC.
Figure 3B:
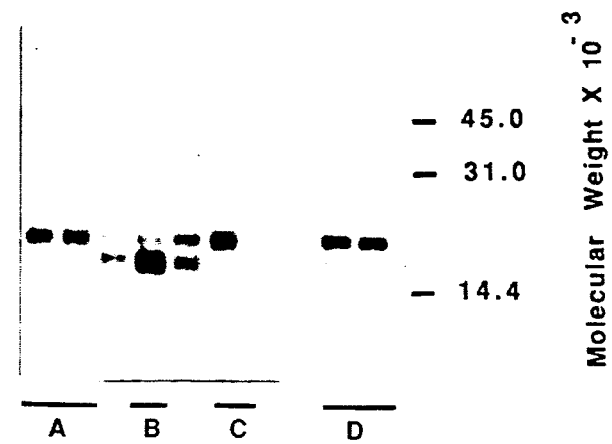
FIG. 3B shows the apparent molecular weights of the subunits as detected by silver staining of reducing SDS polyacrylamide gel electrophoretic analysis.

The HPLC Pool was made 6M in guanidine hydrochloride, 50 mM in ethanolamine and 50 mM in dithiothreitol to reduce the disulfide bonds. The reduced sample was diluted at least 2 fold with either water or 0.05% trifluoroacetic acid in water and loaded onto an analytical C-18 HPLC column equilibrated with a buffer comprising, by volume, 70% Buffer A and 30% Buffer B, as described previously (Buffer A is 0.05% trifluoroacetic acid in water and Buffer B is 0.025% trifluoroacetic acid in acetonitrile). Bound proteins were eluted using a linear gradient of 30% to 60% acetonitrile in 60 minutes. Four prominent peaks of protein, designated A, B, C and D, were detected by monitoring UV absorbance at 229 nm; these eluted within the concentrations of 40% to 47% acetonitrile (see FIG. 3A). When analyzed by reducing SDS gel electrophoresis followed by silver staining, the reduced subunit A migrated within the molecular weight range of 17,500–19,000 daltons, the reduced subunit B migrated within the molecular weight range of 16,000–17,500, the reduced subunit C migrated within the molecular weight range of 17,500–19,000 and the reduced subunit D migrated within the molecular weight range of 17,500–19,000 (see FIG. 3B).

EXAMPLE 4

Amino Acid Sequences of Bovine Osteogenically Active Proteins P3 OF 31-34

The isolated reduced subunits purified from HPLC Pool as disclosed in Example 3, were analyzed by a gas phase sequenator (Applied Biosystems, Model 470A), and found to have the following amino-terminal sequences:

SEQ ID NO: 7
  Subunit A: SAPGRRRQQARNRSTPAQDV

SEQ ID NO: 8
  Subunit C: SXKHXXQRXRKKNNN

SEQ ID NO: 9
  Subunit D: STGGKQRSQNRSKTPKNQEA where the amino acids are represented by the well known one-letter and three-letter designations presented in Table 2 below.

TABLE 2

| Amino Acid | Three-Letter Abbreviation | One-Letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Undetermined | | X |

The isolated subunit B yielded no detectable amino-terminal sequence. When subunit B was digested with Staph V8 protease, and rechromatographed by HPLC, two detectable internal fragments were isolated having the following amino acid sequences:

SEQ ID NO: 10
  Subunit B/Staph V8: XVVLKNYQDMV

SEQ ID NO: 11
  Subunit B/Staph V8: XXKVVLKNYQDM where X represents an unassigned amino acid.

The isolated, reduced subunits purified from HPLC Pool (Example 3) were adsorbed onto polyvinylidine difluoride (PVDF) transfer membrane (Millipore, Bedford, Mass.), exposed to vapors from 80 mg/ml CNBr in 70% formic acid for 15 to 20 hours and sequenced using the gas phase sequenator. The following amino acid sequences are represented by the well-known one-letter designations presented in Table 2.

Subunit A, following cleavage with CNBr, yielded sequences from the simultaneous sequences of several fragments corresponding to the amino terminal sequence:

SEQ ID NO: 12
  ANt: SAPGRRRQQARNRSTPAQDV and three internal fragments:

SEQ ID NO: 13
  A1: NPEYVPKXXXAPTKLNAISV

SEQ ID NO: 14
  A2: XATNXAIVQXLVXLM

SEQ ID NO: 15
  A3: XVXAXG

Subunit B, following cleavage with CNBr, yielded sequences from the simultaneous sequencing of two internal fragments:

SEQ ID NO: 16
  B1: LYLDENEK

SEQ ID NO: 17
  B2: VVEGXGXR when compared with the sequences of fragments of subunit B cleaved with staph V8 protease, fragments B1 and B2 contain overlapping regions, allowing an extended internal sequence in subunit B:

```
           B1: LYLDENEK (SEQ ID NO: 16)
    Staph V8:    XXKVVLKNYQDM (SEQ ID NO: 11)
    Staph V8:     XVVLKNYQDMV (SEQ ID NO: 10)
          B2:                VVEGXGXR (SEQ ID NO: 17)
   Consensus: LYLDENEKVVLKNYQDMVVEGXGXR (SEQ ID NO: 18)
```

Subunit D, following cleavage with CNBr, yielded sequences from the simultaneous sequencing of several fragments corresponding to the amino terminal sequence:

SEQ ID NO: 19
  DNt: STGGKQRSQNRSKTPKNQEA and an internal sequence:

SEQ ID NO: 20
  D1: XATNHAIVQTLVHFINXETV

The isolated reduced subunit C, purified from the HPLC Pool (Example 3), was adsorbed onto a PVDF transfer membrane, subjected to 20 cycles of amino terminal sequencing using the gas phase sequenator, subjected to cleavage by CNBr vapors, and then sequenced using the gas phase sequenator. Subunit C, following cleavage with CNBr, yielded the following internal sequences:

SEQ ID NO: 21
C1: LYLXEYDXVVLXNYQ

SEQ ID NO: 22
C2: SAXXHXIVQT

The amino terminal and internal sequences of subunits A, B, C and D derived from bovine bone can be aligned with homologous regions from the deduced amino acid sequences of cDNA clones encoding the polypeptides designated BMP-2A, BMP-2B and Vgr-1. (Wozney, et al., Science, Vol. 242, pp. 1528–1534 (1988) and (Lyons, et al., Proceedings of the National Academy of Sciences of the U.S.A., Vol. 86, pp. 4554–4558, 1989). Comparison of the similarities and differences of the sequences of subunits B and C and the sequences of BMP-2A and BMP-2B indicate that bovine subunit B shares the same sequence as BMP-2A while bovine subunit C shares the same sequence as BMP-2B. The amino terminus of mature B is inferred from alignment of the human BMP-2A sequence with the amino acid sequences of bovine A, B, C and D, and the presence of a blocked amino terminal on bovine subunit B as described above, presumably resulting from cyclization of an N-terminal glutamine to form a non-sequenceable pyroglutamic acid. Alignment of the sequences of subunit A with those of Vgr-1 indicates a 90% homology.

EXAMPLE 5

Subunit Compositions of Purified Osteogenically Active Proteins P3 OF 31-34

Figure 4A:
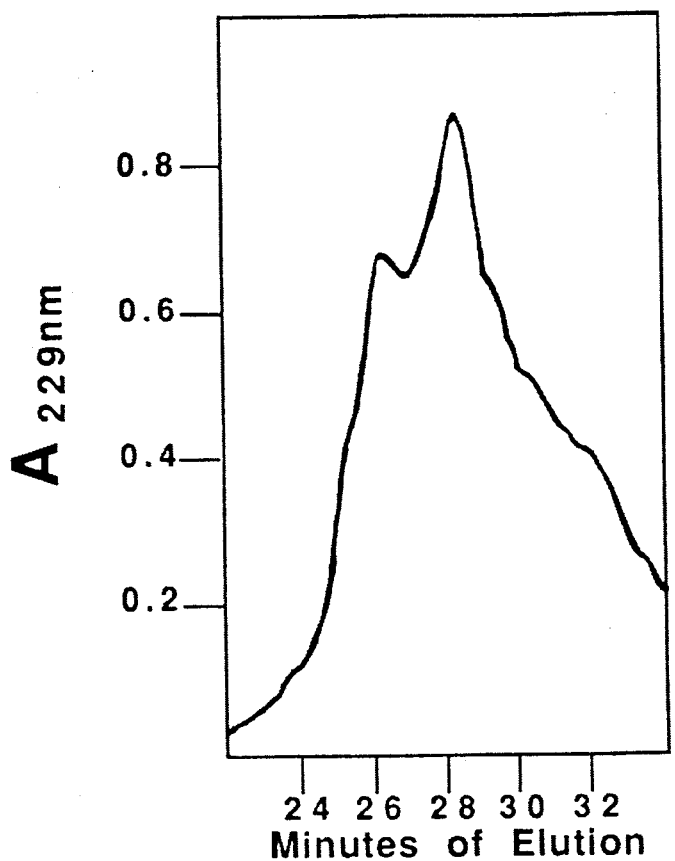
FIG. 4A represents the elution profile obtained by high performance liquid chromatography, on a reverse phase C18 column, of the PS Pool.
Figure 4B:
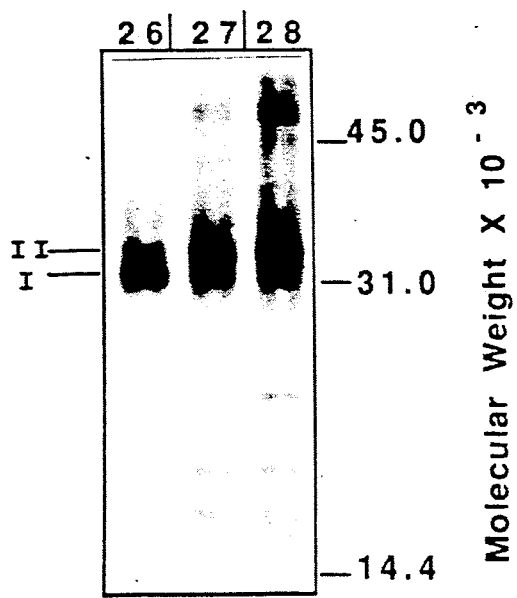
FIG. 4B shows non-reducing SDS polyacrylamide gel electrophoresis of P3 OF 31-34 proteins eluting in fractions 26, 27 and 28 from the reverse phase HPLC of the PS Pool.

Individual fractions, eluting within the HPLC pool (Example 1) and containing the osteogenically active proteins P3 OF 31-34 (FIG. 4A), were analyzed by SDS polyacrylamide gel electrophoresis in the absence of reducing reagents (FIG. 4B). FIG. 4A shows the elution profile obtained by high performance liquid chromatography, on a reverse phase C18 column of the PS Pool. FIG. 4B shows non-reducing SDS polyacrylamide gel electrophoresis of P3 OF 31-34 proteins eluting in fractions 26, 27 and 28 from the reverse phase HPLC of the PS Pool. These individual fractions were further analyzed (as described in Example 3) by reduction of the disulfide bonds with 50 mM dithiothreitol in 50 mM ethanolamine and 6 M guanidine hydrochloride and chromatography on a C18 HPLC column (FIG. 5). FIG. 5A shows the isolation and identification of subunits of the P3 of 31-34 proteins eluting in fraction 26 from the reverse phase HPLC of the PS Pool, while FIG. 5B shows the isolation and identification of P3 OF 31-34 proteins eluting in fraction 28. Subunits A, B, C and D are designated by the solid lines in the figures. Fraction 26, the sample comprising the lowermost band of the P3 OF 31-34 region (Band I of FIG. 4B), was found to contain predominantly subunits B and D with smaller amounts of subunits A and C. Fraction 28, the sample comprising predominantly the uppermost band of the P3 OF 31-34 region (Band II of FIG. 4B), together with a small amount of Band I, was found to contain increased amounts of subunits A and C, and a decreased amount of subunit D.

These individual fractions, eluting within the HPLC pool and containing the osteogenically active proteins P3 of 31-34, Were electrophoresed on 12.5% SDS polyacrylamide gels in the absence of reducing reagent (-DTT), electrophoretically transferred to polyvinylidine difluoride (PVDF) transfer membranes in the presence of 10% methanol, 10 mM cyclohexylamino-1-propanesulfonic acid, pH 10-11, at 0.5 amp for 15 to 30 minutes, and visualized by staining with Coomassie Brilliant Blue R250. Individual protein bands in the region of P3 OF 31-34 defined here as Band I (lower) and Band II (upper), were sliced from the membrane and subjected first to N-terminal sequencing, and then to internal sequencing following treatment with CNBr as described in Example 4. These procedures revealed the following sequence for Band I and II:

| Band Sequenced | Sequences | Subunit Identity |
|---|---|---|
| Band I Internal | XATNXAIVQTL (SEQ ID NO: 23) | D |
| | LYLDEXEXVVL (SEQ ID NO: 24) | B |
| Band II N-Terminal | XXXGRXRQ (SEQ ID NO: 25) | A |
| | XXGGXQR (SEQ ID NO: 26) | D |
| Band II Internal | LYLDXNXXVVLXN (SEQ ID NO: 27) | B |
| | XPEXVPX (SEQ ID NO: 28) | A | where the amino acids are represented by the well-known one-letter designations presented in Table 2.

These results indicated that Band I, the lowermost band of the P3 OF 31-34 proteins, contains predominantly subunits D and B, and that Band II, the uppermost band of the P3 of 31-34 proteins, contains predominantly subunits A and B. These compositions, as well as the observation that these subunits are purified as disulfide-linked dimers in the purified P3 OF 31-34 proteins (Example 3), indicate that subunits D and B may be disulfide-linked as a heterodimer, and that subunits A and B may be disulfide-linked as another heterodimer.

EXAMPLE 6

Osteogenic Compositions for Implantation

The osteogenic preparations of the invention may be used to prepare osteogenic compositions for implantation into mammals. The osteogenic protein may be admixed with one or more of a variety of physiologically acceptable matrices. Such matrices may be resorbable, non-resorbable or partially resorbable. Resorbable matrices include polylactic acid polycaprolactic acid, polyglycolic acid, collagen, plaster of paris and a variety of thermoplastic polymer materials. Non-resorbable materials include hydroxyapatite and partially resorbable materials include matrices such as tricalcium phosphate. The osteogenic protein may be adsorbed onto the matrix material which can be either in a granular or solid form. The osteogenic composition may then be dried by lyophilization.

EXAMPLE 7

Device Coated With Osteogenic Preparations

In this example, the Prep HPLC Pool of Example 1 containing the osteogenically active proteins was used to form osteogenically active devices useful for the healing of bone defects. The devices were prepared by absorbing the Prep HPLC Pool onto solid delivery matrices comprising either a porous hydroxyapatite disc (Interpore 200, Interpore International, Irvine, Calif.) or a porous polylactic acid disc (DRILAC, OSMED Incorporated, Costa Mesa, Calif.). The discs were 8 to 10 mm in diameter and 3 mm thick and were coated with 0.2 to 0.3 mg of the Prep HPLC Pool which was dried onto the matrix by lyophilization. The device may then be sterilized by gamma-irradiation with as much as 3.3 to 3.5 M rads or other suitable means. The devices comprising the osteogenic preparation and the matrix were implanted into trephine defects created in New Zealand Albino Female rabbits, weighing 2.5 to 3.0 kg. Specifically, test devices either coated with the osteogenic preparation or not coated with the osteogenic preparation were surgically implanted into the calvaria using appropriate aseptic surgical techniques. Animals were anesthetized with an intramuscular injection of Ketamine and Xylazine. Following a midline incision, the calvarium was exposed and two trephine holes (one on each side of the midline) 5 mm posterior to the orbits, 8–10 mm in diameter and to the depth of the dura were cut into the calvarium. Trephine defects were created using a Stille cranial drill, exercising great care not to injure the dura. A test device was implanted into one trephine hole while the trephine hole on the opposite side was left empty. Following surgical implantation, antibiotic prophylaxis with penicillin and streptomycin was administered. The animals were followed daily by clinical observations. At explant, the calvaria was removed en block. The specimens were fixed in 10% buffered formalin, decalcified and processed for hematoxylin and eosin stained sections. Histomorphology and qualitative determination of percent ossification was determined by examination of the stained sections (see Table 3 below). The percent area of activity is estimated by eye from the fields of view, or fraction of fields of view, of newly formed bone matrix as compared to the total fields of view not occupied by the matrix in the entire full cross section.

TABLE 3

% OSSIFICATION IN DEVICES IMPLANTED INTO RABBIT TREPHINE DEFECTS

| Test Device | Time of Explant | |
|---|---|---|
| | 6 weeks | 12 weeks |
| Uncoated Hydroxyapatite | <10% | <25% |
| Uncoated Polylactic Acid | <10% | <10% |
| Hydroxyapatite Coated with Osteogenic Preparation | >90% | >90% |
| Polylactic Acid Coated with Osteogenic Preparation | >90% | >90% |
| Hydroxyapatite Coated with Osteogenic Preparation and Treated with Gamma-Irradiation | >75% | >90% |

EXAMPLE 8

Polyclonal Antisera Against Osteogenically Active Proteins P3 OF 31-34

Antisera specific for proteins containing subunits A or D were generated against the synthetic peptides obtained from Peninsula Laboratories, Belmont, Calif. The synthetic peptides comprised branched lysine heptamers to which were linked either eight peptides having the amino acid sequence set out in SEQ ID NO: 29 or eight peptides having the amino acid sequence set out in SEQ ID NO: 30. The peptides were linked to the heptamers by their carboxy termini.

| Antigen | | Antibody Designation |
|---|---|---|
| SEQ ID NO: 29 Subunit A | SAPGRRRQQARNRSTPAQDV | AbANt |
| SEQ ID NO: 30 Subunit D | STGGKRRSQNRSKTPKNQEA | AbDNt |

Antisera were generated in rabbits (3- to 6-month-old New Zealand white male) using standard procedures of subcutaneous injections, first in complete Freunds adjuvant, and later (at 14 and 21 days) in incomplete Freunds adjuvant followed by bleeding and preparation of antisera.

The AbANt and AbDNt antisera were cross-reactive with the synthetic peptide antigens when used in an ELISA format as described in Example 14, and the reduced subunits A and D when used in a Western Blot format as described in Example 13. The AbANt and AbDNt antisera were also cross-reactive with the osteogenically active proteins P3 OF 31-34 when used in either an ELISA or Western Blot format. These antisera were not cross-reactive with any presently defined form of subunit B or subunit C as determined by Western Blot analysis against purified subunit B and subunit C.

A fusion protein of E. coli ribolukinase fused to the 129 amino acid sequence of the carboxy-terminal region of BMP-2A (Wozney, et al., Science, 242, 1528–1534 (1988)) was constructed, expressed and purified essentially as described by Lai, et al., PCT/US86/00131. A synthetic gene encoding the polypeptide designated BMP-2A and the 15 amino acid residues preceding this sequence (Wozney, et al., Science. 242, 1528–1534 (1988)) was constructed using oligonucleotides designed with codons preferred by E. coli. This synthetic gene was cloned into a derivative of the pING1 vector, thereby yielding a fusion protein of ribulokinase fused to the 129 amino acid sequence of the carboxy terminal region of BMP-2A (homologous to subunit B). This construct was transformed into E. coli strain MC1061 and, following induction with 0.5% arabinose, yielded the ribulokinase-B fusion protein produced in inclusion bodies. Inclusion bodies were isolated and extensively washed, yielding a purified preparation of the ribulokinase-B fusion protein.

Antisera specific for subunit B were generated by formic acid cleavage of the ribulokinase-B fusion protein to produce separate ribulokinase and subunit B proteins. The fusion protein was cleaved using 70% formic acid at 37° C. for 48 to 72 hours. The acid-cleaved proteins were lyophilized, reduced, and carboxymethylated. The subunit B was isolated by passage through a Q-Sepharose column equilibrated at 50 mM MES pH 6.5, 6M urea, conductivity 10 mS/cm; and then binding to an S-Sepharose column using the same MES buffer. The subunit B bound to the S-Sepharose and was eluted by 1.0 M NaCl, desalted, and further purified on reverse-phase HPLC eluting in the range 35 to 45% acetonitrile. The isolated subunit B was injected into rabbits as described above. This antisera is designated AbB. The AbB antisera was cross reactive with the isolated B subunit and with the osteogenically active proteins when used in a Western format, as described in Example 13. This antisera was not cross reactive with any presently defined form of subunit A or D as determined by Western Blot.

EXAMPLE 9

Cloning of cDNA For Human Subunit D

A variety of techniques can be used to identify sequences of human DNA encoding proteins homologous to a particular sequenced protein. Such methods include the screening of human DNA, human genomic libraries and human cDNA libraries. A variety of oligonucleotide probes can be used including probes exactly complementary to the human DNA sequence, mixtures of probes complementary to all or some of the possible DNA sequences coding for the particular protein sequence, degenerate probes synthesized such that all possible sequences complementary to all possible DNA sequences coding for the particular protein sequence are represented, and degenerate probes synthesized using nucleotide analogues such as deoxyinosine triphosphate. In this example, the polymerase chain reaction (PCR) technique was used to amplify sequences of human cDNA encoding proteins homologous to subunit D of bovine osteogenically active preparations P3 OF 31-34.

Preparation of cDNA From U-2 OS Cells

The human osteogenic sarcoma cell line U-2 OS was obtained from the ATCC (American Type Culture Collection, Rockville, Md.) and maintained in McCoy's 5a medium supplemented with 10% fetal calf serum and 1% glutamine/penicillin/streptomycin. Unless otherwise described, DNA manipulations, definition of terms, and compositions of buffers and solutions are described by Maniatis, T., et al., *Molecular Cloning: A Laboratory Manual* (1982). Poly (A)+ RNA was isolated from U-2 OS cells using the Fast Track-mRNA isolation kit from Invitrogen (San Diego, Calif.). A first strand cDNA copy of the mRNA was generated with oligo (dT) as the primer using the AMV Reverse Transcriptase System I from Bethesda Research Laboratories (BRL, Gaithersburg, Md.). Each reaction used 1 μg of poly (A)+ RNA which was reverse transcribed into first strand cDNA that was used as template in eight separate polymerase chain reaction (PCR) DNA amplification reactions. Following cDNA synthesis, RNA was hydrolyzed by treatment with 50 mM NaOH at 65° C., followed by neutralization in 0.2 N HCl.

PCR Amplification

Polymerase chain reaction (PCR), as described in R. K. Saiki, et al., Science 239:487-491 (1988), was used to amplify DNA from U-2 OS cDNA prepared as described above. Oligonucleotide primers for PCR were synthesized on an automated DNA synthesizer and were derived from the amino terminal and internal amino acid sequences of bovine subunit D. The 5' PCR primer, designated ODM-1, corresponded to sequence set out in SEQ ID NO: 31 of the first 11 amino acids from the amino terminus of bovine subunit D, namely STGGKQRSQNR. This 32-mer contained all possible combinations of nucleotide sequence coding for this sequence of amino acids and was greater than 4-million-fold degenerate. The nucleotide sequence of ODM-1 was

SEQ ID NO: 32
5'-[T/A][C/G]NACNGGNGGNAA

[G/A]CA[G/A][C/A]GN[T/A]

[C/G]NCA[G/A]AA[C/T][C/A]G-3'.

Bracketed nucleotides are alternatives, and "N" means all alternatives (A, C, T and G).

The 3'PCR primer corresponded to an internal sequence of bovine subunit D set out in SEQ ID NO: 33, NHAIVQTLVHFIN, and was synthesized as the inverse and complementary sequence. This oligonucleotide primer was designated ODB-1 and had the sequence

SEQ ID NO: 34
5'-TTTTTTTTGGATCC[G/A]TTXAT[G/A]

AA[G/A]TGXACXA[G/A]XGT[C/T]TGXACXAT

XGC[G/A]TG[G/A]TT-3'.

Bracketed nucleotides are alternatives, and "X" represents the nucleotide analog deoxyinosinetriphosphate (dITP), which was used in all positions where all four of the nucleotides (A, C, T or G) were possible. (In the Sequence Listing for SEQ ID NO: 34 incorporated herewith, dITP is designated as "N.") The sequence is preceded on the 5' end by a string of eight T's, followed by the sequence GGATCC which designates a BamHI recognition site, leaving a stretch of 39 nucleotides corresponding to the internal amino acid sequence of bovine subunit D.

Amplification of DNA sequences coding proteins homologous to bovine subunit D using these two primers was accomplished using the Perkin-Elmer Cetus Gene Amp DNA Amplification Reagent Kit (obtained either from Parkin-Elmer Cetus, Norwalk, Conn., or United States Biochemical Corporation, Cleveland, Ohio). The PCR reaction contained 1 μg of each primer ODM-1 and ODB-1, ⅛ of the synthesized U-2 OS first strand cDNA (approximately 25-50 ng), 200 micro M of each dNTP, and 2.5U Ampli-Taq DNA Polymerase in the kit-supplied reaction buffer of 50 mM KCl, 1.5 mM MgCl$_2$, 0.1% (w/v) gelatin. PCR was performed for 30 cycles consisting of 1.5 minutes denaturation at 94° C., 2 minutes annealing at 50° C. and 3 minutes elongation at 72° C. After the 30 cycles, a final 10-minute elongation at 72° C. is performed.

The PCR products were analyzed by agarose gel electrophoresis, which revealed a major band of amplified DNA of approximately 300 bp. A Southern Blot was performed in which the DNA in the gel was transferred to a Nytran nylon mmmbrane (Schleicher and Schuell, Keene, N.H.) using an LKB Vacugene Vacuum Blotting Unit, and then the DNA was UV-cross-linked to the membrane using a Stratalinker (Stratagene, LaJolla, Calif.). The membrane was probed for amplified sequences encoding proteins homologous to bovine subunit D using a probe corresponding to the amino acid sequence set out in SEQ ID NO: 35, KTPKNQEALR. This sequence is found near the amino terminus of bovine subunit D, following the sequence used to construct the 5' PCR primer. This probe would therefore hybridize to amplified sequences that encode proteins homologous to bovine subunit D without overlapping either of the two primers used in the amplification. This 29-mer probe was designated ODibb and had the sequence

SEQ ID NO: 36
AAXACXCCXAA[G/A]AA[C/T]CAXGA[G/A]GC

X[C/T]TX[C/A]G where bracketed nucleotides are alternative and "X" represents dITP, which was used in positions where all four nucleotides (A, C, T or G) were possible. (In the Sequence Listing for SEQ ID NO: 36 incorporated herewith, dITP is designated as "N.") The Southern Blot was prehybridized at 42° C. in 5xSSPE (SSPE=0.18 M NaCl, 0.01 M NaH$_2$PO$_4$, 0.001 M EDTA, pH 7.4), 0.5% SDS, 3x Denhardt's, 100 µg/ml salmon sperm DNA, then hybridized at 42° C. in 6xSSPE, 0.5% SDS to the ODibb probe which had been radioactively labelled using polynucleotide kinase and γ[$^{32}$P]ATP. The blot was washed at 42° C. in 2xSSC (SSC=0.15 M NaCl, 0.015 M Na Citrate, pH 7.0), 0.1% SDS. Autoradiography of the blot showed that ODibb hybridized specifically to the 300 bp PCR-amplified DNA.

5' phosphates were added to the blunt-ended PCR product using kinase and ATP, and the DNA was then ligated into the SmaI cut (blunt end) site of the vector pT7T3 18U (Pharmacia, Piscataway, N.J.). Following digestion with SmaI to linearize any relegated vector, the recombinant plasmid DNA was used to transform E. coli TGI cells. Several transformants were picked and used to purify plasmid DNA by a minilysate procedure. The size of the insert contained in these plasmids was confirmed to be 300 bp by restriction analysis.

Cloned cDNAs from seven different transformants were sequenced by dideoxy sequencing methods (Sequenase, United States Biochemical Corp.). The sequences of three of these clones were identical to each other and, when translated to amino acid sequence, it was confirmed that they were homologous to the sequence of bovine subunit D.

Cloning and Nucleotide Sequence of cDNA for Human Mature D cDNA libraries were constructed from poly (A)+ RNA isolated from the human osteosarcoma cell line U-2 OS in λgt10 vectors. Libraries were constructed using oligo (dT) as primer, using kits obtained either from Amersham (cDNA) Synthesis System Plus and cDNA Cloning System λgt10) or Invitrogen (The Librarian X) according to manufacturers' protocols. A total of approximately 850,000 recombinant plaques generated in two libraries were screened with a [$^{32}$P]dCTP-labeled random-primer generated probe designated OD. This OD probe was an approximately 300 bp fragment of DNA, amplified by PCR from one of the hOD clones, using PCR primers corresponding to the exact sequences from the regions of the original degenerate PCR primers, ODM-1 and ODB-1, which were present in this clone. This OD probe therefore contained at least 214 bp of exact sequence for human subunit D. Duplicate nylon replica filters (Hybond N, Amersham) were hybridized with OD at 60° C. in 6xSSPE, 5xDenhardt's, 0.5% SDS, 0.05 mg/ml sheared salmon sperm DNA for 16 to 40 hours, following a 1 hour prehybridization in the same solution without probe. Filters were washed two to three times for 10 minutes each at room temperature in 2xSSC, 0.1% SDS, followed by successive 1 hour washes at 65° C. in 2xSSC, 0.1% SDS and 1xSSC, 0.1% SDS. Filters were subjected to autoradiography for 1 to 4 days. The OD probe hybridized to several positives which appeared on duplicate filters, three of which were identified by PCR (following plaque purification) to contain sequences corresponding to human subunit D. The DNA inserts contained in these three phage clones were amplified by PCR, essentially as described above, using primers corresponding to the sequence of the λgt10 vector flanking the inserts; namely, λgt10F with the sequence

SEQ ID NO: 37
5'-GAGCAAGTTCAGCCTGGTTAAGTCC-3' and λgt10R with the sequence

SEQ ID NO: 38
5'-TGGCTTATGAGTATTTCTTCCAGGG-3'.

Southern Blots of PCR-amplified DNA were probed with an oligonucleotide probe designated ODUC-1, labeled with [$^{32}$P]ATP and polynucleotide kinase, which corresponds to the reverse and complementary sequence between nucleotides 38 and 67, is specific for the sequence of subunit D, and has the sequence

SEQ ID NO: 39
5'-GTCGCTGCTGCTGTTCTCTGCCACGTTGGC-3'.

The PCR amplified DNA from the longest of these three cDNA clones was subcloned in the plasmid vector pT7T3 18U and sequenced. This clone contained the sequence of the entire coding region corresponding to human mature D. This sequence is shown in FIG. 6 along with the corresponding amino acid sequence.

Cloning of human prepro D

A human placental cDNA library in λgtII (Clontech HL1075b) was screened with the random primer labelled OD probe as described above. One positive hybridizing plaque was identified that was 1.6kb long and this clone was designated pOD601. This clone contained the entire coding region of mature D and most of the coding region of prepro D, but was still short of full length by approximately 240 bp at the 5' end. The remaining sequence encoding the 5' end of prepro D was obtained by PCR amplification essentially as described above, using the primers ODP-Sal:

SEQ ID NO: 40
5'-GAATTCGTCGACATGCACGTGCGCTCA-3' and ODPP-3:

SEQ ID NO: 41
5'-CCATGGCGTTGTACAGGTCCAG-3'.

OPD-Sal introduced a SalI site at the 5' end of prepro D, while ODPP-3 corresponded to the sequence of prepro D near the 5' end of pOD601, encompassing a naturally occurring NcoI site.

EXAMPLE 10

Cloning of cDNA for Human Subunit B Cloning of Human Mature B

DNA comprising the sequence of 342 nucleotides representing human mature B was obtained by PCR amplification of DNA generated by reverse transcription of U-2 OS poly (A)+RNA. The amino terminus of mature B was inferred from alignment of the human BMP-2A sequence with the amino acid sequences of bovine A, B, C, and D, and the presence of a blocked amino terminal on bovine subunit B as described in Example 4, presumably resulting from cyclization of an N-terminal glutamine to form a non-sequenceable pyroglutamic acid.

PCR primers corresponded to the sequences obtained from Wang, et al., PCT US87/01537. The 5' PCR primer (a 27-mer designated OB-NM) encoded amino acids set out in SEQ ID NO: 42, QAKHKQRKR, and had the nucleotide sequence

SEQ ID NO: 43
5'-CAAGCCAAACACAAACAGCGGAAACGC-3'.

The 3' PCR primer (a 37-mer designated OB-CP) encoded amino acids set out in SEQ ID NO: 63, VEGCGCR, and was synthesized as the inverse and complementary sequence, preceded on the 5' end by a stop codon, an SstII site, and a HindIII site. The nucleotide sequence of OB-CP was

SEQ ID NO: 44
5'-AAGCTTCCGCGGCTAGCGACACCCACAACCCTCCACA-3'.

The sequence of PCR-amplified human mature B is shown in FIG. 7 and SEQ ID NOS: 3 and 4 along with the corresponding amino acid sequence.

Cloning of Human Prepro B

Cloning of cDNA encoding prepro B was accomplished by PCR amplification from U2-OS mRNA essentially as described above, except that Vent DNA polymerase (New England Biolabs) was used instead of Taq polymerase, and the denaturation step was carried out at 96° C. The primers used for PCR were OB-PPN:

SEQ ID NO: 45
5'-ACTGTCGACATGGTGGCCGGGACCCG-3' and OB-PPC:

SEQ ID NO: 46
5'-ACGTTTTTCTCTTTTGTGGAGAGGAT-3' which were successfully used to amplify an 850 bp fragment corresponding to the entire coding region of prepo B.

EXAMPLE 11

Construction of Mammalian Expression Vectors for the Production Of Human Subunits B and D Plasmid vectors that contain cDNA genes for subunits B and D were constructed based on vectors originally developed for expression of the antibody heavy chain genes (Better, et al., PCT US89/03842): pING1714 and pING2237N (which is a derivative of pING2227 containing a gene for dhfr selection and a unique NotI site). These vectors have a number of features useful for regulating gene expression in mammalian cells.

Transcriptional activity is controlled by the heavy chain mouse enhancer derived from M13 M8alphaRX12 (Robinson, et al., PCT US86/02269) located adjacent to the mouse Abelson virus LTR promoter/enhancer (Abl) derived from pelin2 (provided by Dr. Owen Witte, UCLA, and described by Reddy, et al., *Proc. Natl. Acad. Sci.* (USA), 80, 3623 (1983)) in pING2237N and by the Abl in pING1714. Downstream of the Abl promoter is the 16S splice donor and acceptor segment from SV40 in both vectors, which was excised from pUC12/pL1 (Robinson, et al., PCT US86/02269). The expressed genes were located just downstream of the splice junction. At the 3' end of the gene in pING2237N, the human genomic gamma-1 polyadenylation sequence has been cloned as a 1187-bp DNA fragment described by Ellison, et al., *Nucl. Acids Res.*, 10, 4071 (1982).

The remainder of the vector is similar to pSV2, containing a selectable marker (neo or dhfr) under the control of the SV40 early promoter and sequences of pBR322 necessary for growth in *E. coli*. Plasmid pING2237N contains a unique NotI site located in the pBR322-derived sequences that was introduced at the unique AatII site by cutting with AatII and ligating the annealed oligonucleotides

SEQ ID NO: 47
5'-TGAAGCGGCCGCAACAGACGT-3' and

SEQ ID NO: 48
5'-CTGTTGCGGCCGCTTCAACGT-3'.

This created a vector that could be linearized with NotI prior to transfection into mammalian cells. The oligonucleotides were chosen, and resulting clones were selected such that the AatII site was regenerated on one side of the NotI site only.

A useful feature of the vector pING1714 (and pING2237N) is that it contains unique SalI and SstII sites into which genes such as those encoding the subunits B and D can be cloned. The SalI site is positioned so that insertion at this site generates a transcriptional fusion controlled by the enhancer/promoter region. The SstII site is located in the CH3 domain of the heavy chain gene.

Construction of Vectors for Expression of Subunits B and D in Animal Cells

DNA representing the entire protein region of subunit C (prepro plus mature) and consisting of 1224 nucleotides was obtained by PCR amplification of DNA generated by reverse transcription of U-2 OS poly (A)+ NNA. PCR primers corresponded to the sequences obtained from Wang, et al., PCT US87/01537. The 5' PCR primer (a 37-mer designated OC-NP) encoded amino acids set out in SEQ ID NO: 49, MIPGNRML, and was preceded on the 5' end by a SalI site and an EcoRI site. OC-NP had the nucleotide sequence

SEQ ID NO: 50
5'-GAATTCGTCGACATGATTCCTGGTACCGAATGCTGA-3'.

The 3' PCR primer (a 37-mer designated OC-CP) encoded the amino acid sequence set out in SEQ ID NO: 51, VEGCGCR, and was synthesized as the inverse and complementary sequenced, preceded on the 5' end by a stop codon, an SstII site, and a HindIII site. The nucleotide sequence of OP-CP was

SEQ ID NO: 52
5'-AAGCTTCCGCGGCTCAGCGGCACCCACATCCCTCTACT-3'.

The sequence of PCR-amplified human prepro and mature C is shown in FIG. 8 along with the corresponding amino acid sequence. The amino terminus of mature C is inferred from alignment of the human BMP-2B sequence with the amino terminal sequence of bovine C. The PCR-amplified gene was cut with SalI and SstII and cloned into pING1714. The resulting plasmid pING3900 still contained about 470 bp of DNA from the C-terminal domain of the heavy chain constant region between the end of the C gene and the gamma-1 polyadenylation sequence.

To eliminate these sequences and construct a vector with a unique NotI site, pING3900 served as the template for the construction of two other vectors. A three-piece ligation was performed with the SalI to BolII vector fragment (containing the NotI site) from pING2237N and the SalI to SstII and SstII to BolII fragments from pING3900, generating pING3901. This vector then contained the C gene and a unique NotI site, yet still contained the heavy chain gene segment. To remove this segment, pING3901 was cut with AatII and BamHI and the vector fragment was isolated. Concurrently, pING3901 was cut with AatII and SstII, and the fragment containing the enhancer/promoter, 16S splice and the C gene was purified. The genomic heavy chain polyadenylation region was amplified from pING2237N by PCR with the primers

SEQ ID NO: 53
5'-ACTACCGCGGTAAATGAGTGCGACGG-3' and

SEQ ID NO: 54
5'-CACTGCATTCTAGTTGTGGT-3'.

The former primer introduced an SstII site at its 5' end while the latter primer is located in the vector sequences downstream of the BamHI site. The PCR-amplified fragment was cut with SstII and BamHI, and the three fragments were ligated to generate the plasmid pING3902.

Plasmid pING3902 contains unique SalI and SstII sites and was used to construct mammalian expression vectors for genes encoding subunits B and D. The gene sequences encoding the mature subunits B and D (FIG. 7 and 6, respectively) were amplified by PCR to yield a blunt end at the 5' end and contain an SstII site just following the termination codon of the genes.

Primers

SEQ ID NO: 55
5'-CAAGCCAAACACAAACAGCGGAAACGC-3' and

SEQ ID NO: 56
5'AAGCTTCCGCGGCTAGCGACACCCACAACCCTCCACA-3' were used to amplify the coding sequence for mature B.

Primers

SEQ ID NO: 57
5'-TCCACGGGGAGCAAACAGCGCA-3' and

SEQ ID NO: 58
5'-CATACCGCGGAGCTAGTGGCAGCCACA-3' were used to amplify the coding sequence for mature D. These fragments were each digested with SstII.

Likewise, the prepro C gene segment (ppC) shown in FIG. 8 was amplified from first-strand cDNA from U-2 OS mRNA by PCR with primers

SEQ ID NO: 59
5'-GAATTCGTCGACATGATTCCTGGTAACCGAATGCTGA-3' and

SEQ ID NO: 60
5'-ACGCTTGGCCCTCCGGCGTCGGGTCAA-3' so that it contained a SalI restriction site just upstream of the initiation codon ATG and a blunt end at its 3' end. This fragment was digested with SalI.

A three piece ligation with the prepro C gene fragment, the mature B gene fragment and the purified vector fragment of pING3902, resulting from digestion with SalI and SstII, yielded plasmid pING3904 containing the ppC-mature B gene.

A three piece ligation with the prepro C gene fragment, the mature D gene fragment and the purified vector fragment of pING3902, resulting from digestion with SalI and SstII, yielded plasmid pING3906 containing the ppC-mature D gene.

Construction of Vectors with an Alternate Drug Resistance Gene

Additional vectors were constructed for mammalian gene expression that differ from those described above, only in the selectable drug resistance gene. Plasmid pING3005 is similar to pING1714 except that it contains the xanthine-guanine phosphoribosyl transferase (gpt) gene instead of the neomycin phosphotransferase gene (neo). Plasmid pING3906 was cut with BolII, treated with calf intestinal alkaline phosphatase (CIAP), cut with SalI, and the vector fragment was purified. Plasmid pING3005 was cut with BamHI plus BolII, and the DNA fragment containing the gpt gene was purified.

These two fragments were ligated to the purified B and D gene fragments from pING3904 and pING3906, respectively, that had been excised with BamHI, treated with CIAP, and cut with SalI. These ligations generated plasmids pING3918 (B) and pING3919 (D) both containing the gpt selectable marker.

These plasmids were transfected into mammalian cells along with vectors containing the neo marker either together or sequentially to generate cell lines producing combinations of heterologous genes.

Construction of Vectors for the Expression of B and D With Homologous Prepro Sequences To construct prepro B-mature B expression vectors, the 850 bp fragment corresponding to prepro B described above was digested with SalI, a site introduced by the 5' PCR primer, and NcoI, a site within the prepro sequence; the resulting 680 bp fragment was purified. To obtain a fragment containing the remainder of the prepro and the mature sequence of B, a DNA fragment was PCR amplified from U2-OS mRNA using the primers PPOB-2, located upstream of the NcoI site SEQ ID NO: 61
(primer sequence 5'-TTTTTTCCAGT

CTTTTGGACACCAGGTTGG-3'), and OB-CP, which introduced an SstII site at the end of the mature region SEQ ID NO: 62
(primer sequence 5'-AAGCTTCCGCGGCTAG

CGACACCCACAACCCTCCACA-3').

This fragment was digested with NcoI and SstII and purified. A 3-piece ligation was performed with the SalI-NcoI and NcoI-SstII fragments just described and the SalI -SstII vector fragment from pING3920 (identical to the corresponding vector segment from pING3902) to generate pING4207 (gpt gene). To construct a vector with dhfr instead of gpt, the ClaI-DraIII fragment of pING4207 containing the entire B gene was cloned into the ClaI-DraIII vector fragment of pMB27, a vector essentially similar to pING3902 except that it contained the dhfr gene. The resulting construct was called pING4206.

To construct prepro D- mature D expression vectors, the following 4 fragments were ligated together: (1) the 270 bp SalI-NcoI fragment from the 5' end of prepro D, generated by PCR using primers ODP-Sal and ODPP-3 as described above; (2) an 850 bp NcoI-AlwNI fragment from the cDNA clone pOD601; (3) a 150 bp AlwNI-SstII fragment corresponding to the end of mature D excised from pING3919; and (4) the SalI-SStII vector fragment from pING3920. The resulting vector was designated pING4120 and had gpt marker.

To construct a single vector for the simultaneous coexpression of B and D, plasmid pING4206 (B gene) was linearized at the unique AatII site and ligated to an AatII fragment from pING4120 containing the entire D gene, yielding the 2-gene vector pING4121 (dhfr).

EXAMPLE 12

Expression of Human Osteogenically Active Proteins from Animal Cells

According to this example, various osteogenically active proteins were expressed from animal cells including B and D monomers, B/B and D/D homodimers and the B/D heterodimer.

Stable Transfection of CHO K-1 Cells for the Production Of Homodimers of Human Subunits D or B The cell line CHO K-1 (ATCC CRL 61) was grown in Ham's F12 medium plus 10% fetal bovine serum. The medium is supplemented with glutamine/penicillin/streptomycin Irvine Scientific, Irvine, Calif.).

The cells were transfected using the calcium phosphate method of Wigler, et al., Cell, 11, 223 (1977). Following the calcium phosphate treatment, the cells are plated in T150 flasks, and transfectants were obtained by growth in the presence of selective medium. Untransformed cells were removed during successive feedings with selective medium and, at 10 days to 2 weeks, only microcolonies of transfected cells were observed. G418 selection was used at 0.6 mg/ml. Mycophenolic acid was used at 24 µg/ml plus 0.25 mg/ml xanthine.

Cell lines producing subunit D or B were obtained as described below. The expression plasmids pING3906 or pING3904 was digested with NotI and transfected separately into the CHO K-1 cells to yield G418-resistant cells. The transfectants were grown in T-flasks, trypsinized and subcloned. The subclones were screened for the presence of D-specific or B-specific messenger RNA isolated as described by White, J. Biol. Chem., 257, 8569 (1982) or Gough, Anal. Biochem. 173, 93 (1988), and probed on slot blots with $^{32}$[P]-labeled D-specific or B-specific DNA.

Those cell lines that were identified as producing the highest levels of mRNA were expanded and grown in Ham's F12 medium containing 10% FBS and then shifted into serum-free (HB-CHO, Irvine Scientific) or protein-free medium (PFHM, Gibco) for the production of D or B.

Stable Transfection of CHO K-1 Cells for the Production of Mixtures of Human Subunits D and B According to the invention, cell lines to be transformed with genes encoding both subunit B and subunit D can be transformed according to a variety of methods including, but not necessarily limited to (1) co-transformation with two genes on two vectors at once (2) sequential transformation first with one gene and then another; and (3) transformation with two genes on the same vector.

To obtain cell lines which produce mixtures of subunits D and B, clones of D-producing transfectants which were transfected with the plasmid containing the neo selectable marker (pING3906) were transfected according to the calcium phosphate method with the plasmid constructed with the gpt selective marker containing the gene encoding the B subunit (pING3918). G418- and MPA-resistant transfectants were then screened for the production of B- and D-specific mRNA. Cell lines that expressed both mRNAs were grown in large volumes in Ham's F12 plus 10% FBS and then shifted into serum-free or protein-free medium for the purpose of producing B/D dimers. One such cell line has been designated C1131.

An alternative method to obtain cell lines which produce mixtures of subunits B and D, involved co-transfection of NotI-digested pING3904 and pING3906 into CHO cells to give G418-resistant cells. Transfectants were grown in T-flasks, trypsinized and subcloned. The subclones were screened for the presence of B- and D-specific messenger RNA. Those cell lines that produce both messages were scaled up for the production of B/D dimers.

Stable Transfection of Mouse Lymphoid Cells For the Production of Homodimers of Human Subunits B or D, and a Mixture of Subunits B and D The cell line Sp2/0 (American Type Culture Collection CRL 1581) was grown in Dulbecco's Modified Eagle Medium plus 4.5 g/l glucose (DMEM, Gibco) plus 10% fetal bovine serum. The medium was supplemented with glutamine/penicillin/streptomycin (Irvine Scientific, Irvine, Calif.).

The electroporation method of Potter, et al., Proc. Natl. Acad. Sci. (USA), 81, 7161 (1984) was used. After transfection, cells were allowed to recover in complete DMEM for 24 to 48 hours, and then seeded either into 96-well culture plates at 10,000 to 50,000 cells per well or in T-flasks at $5 \times 10^4$ cells/ml in the presence of selective medium. G418 (Gibco) selection was used at 0.8 to 1.2 mg/ml. Mycophenolic acid (MPA, Calibiochem) was used at 6 µg/ml plus 0.25 mg/ml xanthine. The electroporation technique gave a transfection frequence of 1 to $10 \times 10^{-5}$ for the Sp2/0 cells.

Cell lines producing subunit D were obtained as described below. The expression plasmid pING3906 (containing the neo selectable marker) was digested with NotI and transfected into the Sp2/0 cells. Approximately 75% of the cells were plated into 96-well plates. The remaining 25% were plated into T25 or T75 flasks. Clones of D-producing transfectants were screened directly for the presence of D-specific messenger RNA.

Those cell lines that were identified as producing the highest levels of mRNA were expanded and grown either in DMEM medium plus 10% fetal bovine serum or in protein-free medium (PFHM, Gibco) for the production of subunit D. By this strategy, cell lines which produce subunit B or homodimers of subunit B were similarly developed.

To obtain cell lines which produce mixtures consisting of subunits D and B, a D-producing cell line which had been transfected with a plasmid containing the neo selectable marker (pING3906) was subsequently transfected with a plasmid containing the gpt selective marker and the gene encoding the B subunit (ING3918). G418- and MPA-resistant transfectants were then screened for the production of B- and D-specific mRNA. Cell lines that express both mRNAs were grown in serum-free or protein-free medium.

EXAMPLE 13

Detection of Subunits B and D Using Western Blot Assay

Protein samples were electrophoresed on 12.5 or 15% SDS polyacrylamide gels (SDS-PAGE), and electrophoretically transferred to either polyvinylidine difluoride (PVDF) transfer membrane or nitrocellulose in the presence of 10% methanol, 10 mM cyclohexylamino-1-propanesulfonic acid (CAPS), pH 10-11, at 0.5 amp for 15 to 30 minutes. The PVDF membrane or nitrocellulose filter was treated for Western Blot analysis utilizing antibodies generated as described in Example 8.

The PVDF membrane or nitrocellulose paper containing the protein was placed in a solution-designated buffer P (composed of 20 mM phosphate, pH 7.4; 0.15 M NaCl; 0.05% Tween-20; 0.25% gelatin; and 0.02% sodium azide) for a minimum of 1 hour at 22° C. with agitation.

Buffer P was then replaced by buffer Q (composed of buffer P plus antibodies) for a minimum of 1 hour at 22° C. (or overnight at 4° C.). Buffer Q was replaced by buffer P, which was changed four times over a minimum of 1 hour. Buffer P was replaced by buffer R (buffer P plus $^{125}$I protein A at $2.5 \times 10^5$ cpm/ml, Amersham) and incubated for 1 hour at 22° C. with agitation. Buffer R was replaced by buffer P, which was changed at least four times during 1 hour of incubation.

The moist PVDF membrane or nitrocellulose filter was placed between sheets of plastic wrap, and together with a lighting screen and X-ray film (Dupont Cronex, Wilmington, Del.), enclosed in a light-proof folder, and placed at $-70°$ C. for an appropriate period of time. The exposed film was developed using standard techniques and equipment.

EXAMPLE 14

Detection of Subunit B and Subunit D Using Enzyme-Linked Immunosorbant Assay-ELISA ELISA assays were performed in 96-well Immulon plates (Dynatech) into which samples at several dilutions and in a final volume of 200 µl containing 3M urea, 15 mM $Na_2CO_3$, 24 mM $NaHCO_3$ pH 9.6 were bound. Binding was performed first at 60° C. for 15 minutes and subsequently at 21° C. to 24° C. for 2 hours or at 4° C. for 12 to 18 hours in a humidified chamber. Following binding, the wells of the plate were individually washed three times with a solution containing 8 mM $Na_2HPO_4$, 1.5 mM $KH_2PO_4$, 2.7 mM KCl, 137 mM NaCl, and 0.05% Tween-20 in Millipore-filtered, distilled water (solution E), and then washed two times with Millipore-filtered, distilled water.

Antibody against the N-terminal of subunit D (described in Example 8), or against reduced and carboxymethylated subunit B (described in Example 8) were added at a 1:1000 to 1:5000 dilution in solution E and incubated at 21° C. to 24° C. for 2 hours. Following incubation with antibody, the plate was washed as described above and peroxidase-conjugated Goat anti-Rabbit antibody (Cappel) at 1:1000 dilution in solution E was added to the plate and incubated at 21° C. to 24° C. for 2 hours. The plate was washed as described above and developed using the TMB reagent (Pierce) according to the manufacturer's instructions.

Typical assays contained recombinant protein prepared as described in Example 15, a positive control containing aliquots from a single lot of a Prep-HPLC pool of bovine bone (described in Example 1), and appropriate negative controls For purposes of comparison between the various recombinant protein preparations, the B-immunoreactivity and the D-immunoreactivity contained in 50 µg of the Prep HPLC pool of the bovine bone preparation was defined as 2 units of reactivity.

EXAMPLE 15

Characterization of Human Osteogenically Active Proteins Expressed in Animal Cells The osteogenically active proteins contained in the culture supernatant were enriched using column chromatography steps as described in Example 1. For example, the conditioned media was adjusted to 6 M urea, 50 mM MES, pH 6.5, conductivity 10 mS/cm (by addition of crystalline urea and 1 M MES, pH 6.5). The adjusted sample was applied onto a Q-Sepharose column equilibrated in 6 M urea, 50 mM MES, pH 6.5, conductivity 10 mS/cm. The unbound protein of the Q-Sepharose column was applied to a S-Sepharose column equilibrated in 6 M urea, 50 mM MES, pH 6.5, conductivity 10 mS/cm, and the S-Sepharose column was washed with the same buffer to remove unbound protein. The protein bound to the S-Sepharose column was eluted with 6 M urea, 50 mM MES, pH 6.5, 1 M NaCl. Further enrichment was achieved using hydrophobic interaction chromatography on a Phenyl-Sepharose column. The sample in 6 M urea, 50 mM MES, 1 M NaCl was made 50 mM in Tris HCl, pH 7.3-8.0, using 1 M Tris stock, and was 25% saturated in ammonium sulfate using 13.4 g ammonium sulfate for each 100 ml of sample. The sample was applied to a Phenyl-Sepharose column equilibrated in 6 M urea, 50 mM Tris HCl, pH 7.3–8.0, 25% saturated ammonium sulfate, and the column was washed with the same buffer to remove unbound protein. The bound protein was eluted using 6 M urea, 50 mM Tris HCl, pH 7.3 to 8.0 or 6 M urea, 50 mM MES pH 6.5. The sample was desalted and further purified by reverse phase chromatography using C-18 HPLC columns (as shown in Example 1) equilibrated with a buffer containing, by volume, 70% Buffer A and 30% Buffer B, as described previously (Buffer A is 0.05% trifluoroacetic acid in water and Buffer B is 0.025% trifluoroacetic acid in acetonitrile). Bound proteins were eluted using a linear gradient of 30% to 60% acetonitrile. The immunoreactive dimers eluted within the concentrations of 35% to 45% acetonitrile, and were concentrated by lyophilization. Enriched samples isolated from the supernatant of cells transfected with both the gene sequence for human mature B and the gene sequence for human mature D (C11131) are called Prep B/D. Enriched samples isolated from the supernatant of cells transfected only with the gene sequence for human mature B are called Prep B. Enriched samples isolated from the supernatant of cells transfected only with the gene sequence for human mature D are called Prep D. Enriched samples containing admixtures of Prep B and Prep D are called Prep B+D.

Following lyophilization, the enriched samples were solubilized in Millipore-filtered, distilled water and were characterized for the presence of subunit B and/or subunit D using specific antisera (described in Example 8), Western blot techniques (described in Example 13), and ELISA assays (described in Example 14).

Figure 9:
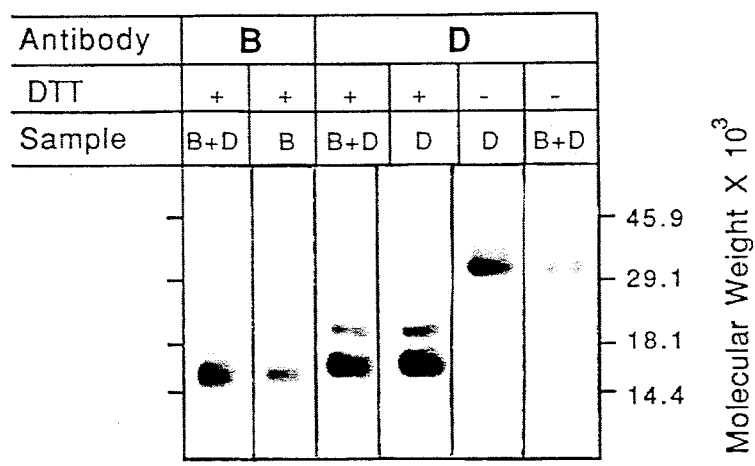
FIG. 9 shows reducing and non-reducing SDS polyacrylamide gel electrophoresis of enriched samples isolated from media of CHO cells transfected with both the gene sequence for human mature B and the gene sequence for human mature D (Prep B/D), or separately transfected with only the gene sequence for human mature D (Prep D), or with only the gene sequence for human mature B (Prep B). Proteins were visualized using autoradiography following Western Blot analysis.

Western Blot analyses of the enriched samples isolated from media of CHO cells transfected with both the B-subunit sequence and the D-subunit sequence (Prep B/D), or separately transfected with only the D-subunit sequence (Prep D), or with only the B-subunit sequence (Prep B) are shown in FIG. 9. The Western blot analysis of the reduced samples performed with antibody specific for subunit B showed, in Prep B/D, a broad B-specific band of 16,000 to 17,000 daltons. Similar analysis of Prep B showed an identical B-specific band. Analysis of reduced samples using D-specific antibody showed a broad D-specific band at 17,000 to 19,000 daltons and a less prominent band at 22,000 to 23,000 daltons for samples of Prep B/D and Prep D. Analysis of non-reduced Prep B/D and non-reduced Prep D with D-specific antibody showed prominent D-containing dimers of 30,000 to 32,000 daltons and less prominent dimers extending to a molecular weight of approximately 37,000 daltons. Poor reactivity of the B-specific antibody with non-reduced Prep B and non-reduced Prep B/D hindered Western blot demonstration of the B-subunit in Prep B and in Prep B/D (data not shown).

Polyacrylamide gel electrophoresis of the proteins contained in individual HPLC fractions of Prep B/D, transfer of the proteins to PVDF membrane (described in Example 13), and Coomassie staining were used to isolate the non-reduced, 30,000 to 32,000 dalton band. The excised band was sequenced using the gas phase sequenator. The sequence obtained revealed the N-terminal sequence STGSKQR-QN of the D-subunit and the N-terminal sequence QAK-KQR--L of the B-subunit (the complete sequences of the D and B subunits are set out in SEQ ID NOS: 2 and 4, respectively).

Figure 10:
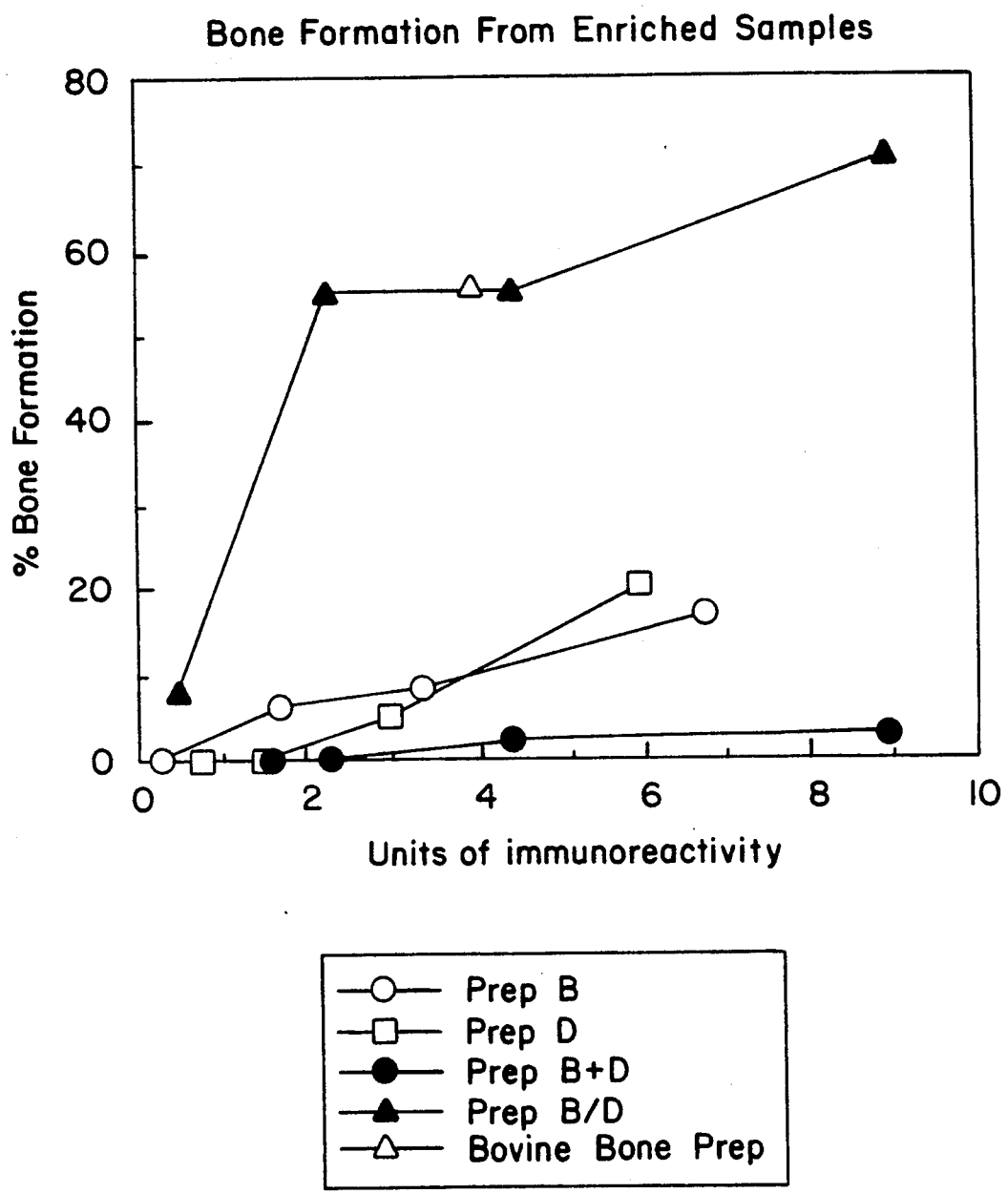
FIG. 10 shows the biological activity of the enriched samples of Prep B/D, Prep B+D, Prep D and Prep B as determined using the rat implant assay following implantation of various amounts of immunoreactivity.

The biological activity of the enriched samples of Prep B/D, Prep B+D, Prep D and Prep B were determined using the rat implant assay as described in Example 2. ELISA assays were used to quantitate the amount of B-subunit or D-subunit immunoreactivity present in each of the enriched preparations. Comparison was made to the amount of B-immunoreactivity and/or the amount of D-immunoreactivity contained in 50 μg of the Prep-HPLC pool of the bovine bone preparation which is defined as 2 units of immunoreactivity. Two units of the Prep HPLC pool of the bovine bone preparation contain 1 unit of B-immunoreactivity and 1 unit of D-immunoreactivity, and, upon implantation for 21 days yielded 14% of the area of the stained sections occupied by osteoid activity. Enriched samples of Prep B/D, Prep B+D, Prep B and Prep D containing various amounts of immunoreactivity were implanted for 17 days and analyzed for percent bone formation in the explant tissue (FIG. 10). The most potent bone formation activity from media of cells was obtained with Prep B/D such as from cell line C1131. For example, implantation of Prep B/D containing 1.5 units B-immunoreactivity and 0.8 units of D-immunoreactivity, resulted in 55% of the area of the stained sections occupied by osteoid activity. In contrast, implantation of Prep B containing 1.5 units of B-immunoreactivity resulted in less that 10% of the area of the stained sections occupied by osteoid activity, implantation of Prep D containing 1.1 units of D-immunoreactivity resulted in only 1% of the area of the stained sections occupied by osteoid activity and implantation of an admixture of Prep B (1.5 units and Prep D (0.8 units) containing a total of 2.3 units resulted in only 1% of the area of the stained sections occupied by osteoid activity.

Numerous modifications and variations in the practice of the invention are expected to occur to those skilled in the art upon consideration of the foregoing descriptions of preferred embodiments thereof. Consequently, only such limitations should be placed upon the invention as appear in the following claims.

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 417 base pairs
( B ) TYPE: nucleic acid
( C ) STRANDEDNESS: single
( D ) TOPOLOGY: linear ( i i ) MOLECULE TYPE: cDNA ( i x ) FEATURE:
    ( A ) NAME/KEY: CDS
    ( B ) LOCATION: 1..417

( x i ) SEQUENCE DESCRIPTION: SEQ ID NO:1:

| TCC | ACG | GGG | AGC | AAA | CAG | CGC | AGC | CAG | AAC | CGC | TCC | AAG | ACG | CCC | AAG | 48 |
|---|---|---|---|---|---|---|---|---|---|---|---|---|---|---|---|---|
| Ser | Thr | Gly | Ser | Lys | Gln | Arg | Ser | Gln | Asn | Arg | Ser | Lys | Thr | Pro | Lys | |
| 1 | | | | 5 | | | | | 10 | | | | | 15 | | |

| AAC | CAG | GAA | GCC | CTG | CGG | ATG | GCC | AAC | GTG | GCA | GAG | AAC | AGC | AGC | AGC | 96 |
|---|---|---|---|---|---|---|---|---|---|---|---|---|---|---|---|---|
| Asn | Gln | Glu | Ala | Leu | Arg | Met | Ala | Asn | Val | Ala | Glu | Asn | Ser | Ser | Ser | |
| | | | 20 | | | | | 25 | | | | | 30 | | | |

| GAC | CAG | AGG | CAG | GCC | TGT | AAG | AAG | CAC | GAG | CTG | TAT | GTC | AGC | TTC | CGA | 144 |
|---|---|---|---|---|---|---|---|---|---|---|---|---|---|---|---|---|
| Asp | Gln | Arg | Gln | Ala | Cys | Lys | Lys | His | Glu | Leu | Tyr | Val | Ser | Phe | Arg | |
| | | 35 | | | | | 40 | | | | | 45 | | | | |

| GAC | CTG | GGC | TGG | CAG | GAC | TGG | ATC | ATC | GCG | CCT | GAA | GGC | TAC | GCC | GCC | 192 |
|---|---|---|---|---|---|---|---|---|---|---|---|---|---|---|---|---|
| Asp | Leu | Gly | Trp | Gln | Asp | Trp | Ile | Ile | Ala | Pro | Glu | Gly | Tyr | Ala | Ala | |
| | 50 | | | | | 55 | | | | | 60 | | | | | |

| TAC | TAC | TGT | GAG | GGG | GAG | TGT | GCC | TTC | CCT | CTG | AAC | TCC | TAC | ATG | AAC | 240 |
|---|---|---|---|---|---|---|---|---|---|---|---|---|---|---|---|---|
| Tyr | Tyr | Cys | Glu | Gly | Glu | Cys | Ala | Phe | Pro | Leu | Asn | Ser | Tyr | Met | Asn | |
| 65 | | | | | 70 | | | | | 75 | | | | | 80 | |

| GCC | ACC | AAC | CAC | GCC | ATC | GTG | CAG | ACG | CTG | GTC | CAC | TTC | ATC | AAC | CCG | 288 |
|---|---|---|---|---|---|---|---|---|---|---|---|---|---|---|---|---|
| Ala | Thr | Asn | His | Ala | Ile | Val | Gln | Thr | Leu | Val | His | Phe | Ile | Asn | Pro | |
| | | | | 85 | | | | | 90 | | | | | 95 | | |

| GAA | ACG | GTG | CCC | AAG | CCC | TGC | TGT | GCG | CCC | ACG | CAG | CTC | AAT | GCC | ATC | 336 |
|---|---|---|---|---|---|---|---|---|---|---|---|---|---|---|---|---|
| Glu | Thr | Val | Pro | Lys | Pro | Cys | Cys | Ala | Pro | Thr | Gln | Leu | Asn | Ala | Ile | |
| | | | 100 | | | | | 105 | | | | | 110 | | | |

| TCC | GTC | CTC | TAC | TTC | GAT | GAC | AGC | TCC | AAC | GTC | ATC | CTG | AAG | AAA | TAC | 384 |
|---|---|---|---|---|---|---|---|---|---|---|---|---|---|---|---|---|
| Ser | Val | Leu | Tyr | Phe | Asp | Asp | Ser | Ser | Asn | Val | Ile | Leu | Lys | Lys | Tyr | |
| | | | 115 | | | | | 120 | | | | | 125 | | | |

| AGA | AAC | ATG | GTG | GTC | CGG | GCC | TGT | GGC | TGC | CAC | | | | | | 417 |
|---|---|---|---|---|---|---|---|---|---|---|---|---|---|---|---|---|
| Arg | Asn | Met | Val | Val | Arg | Ala | Cys | Gly | Cys | His | | | | | | |
| | 130 | | | | | 135 | | | | | | | | | | |

( 2 ) INFORMATION FOR SEQ ID NO:2:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ser | Thr | Gly | Ser | Lys | Gln | Arg | Ser | Gln | Asn | Arg | Ser | Lys | Thr | Pro | Lys |
|---|---|---|---|---|---|---|---|---|---|---|---|---|---|---|---|
| 1 | | | | 5 | | | | | 10 | | | | | 15 | |

| Asn | Gln | Glu | Ala | Leu | Arg | Met | Ala | Asn | Val | Ala | Glu | Asn | Ser | Ser | Ser |
|---|---|---|---|---|---|---|---|---|---|---|---|---|---|---|---|
| | | | 20 | | | | | 25 | | | | | 30 | | |

| Asp | Gln | Arg | Gln | Ala | Cys | Lys | Lys | His | Glu | Leu | Tyr | Val | Ser | Phe | Arg |
|---|---|---|---|---|---|---|---|---|---|---|---|---|---|---|---|
| | | 35 | | | | | 40 | | | | | 45 | | | |

| Asp | Leu | Gly | Trp | Gln | Asp | Trp | Ile | Ile | Ala | Pro | Glu | Gly | Tyr | Ala | Ala |
|---|---|---|---|---|---|---|---|---|---|---|---|---|---|---|---|
| | 50 | | | | | 55 | | | | | 60 | | | | |

| Tyr | Tyr | Cys | Glu | Gly | Glu | Cys | Ala | Phe | Pro | Leu | Asn | Ser | Tyr | Met | Asn |
|---|---|---|---|---|---|---|---|---|---|---|---|---|---|---|---|
| 65 | | | | | 70 | | | | | 75 | | | | | 80 |

| Ala | Thr | Asn | His | Ala | Ile | Val | Gln | Thr | Leu | Val | His | Phe | Ile | Asn | Pro |
|---|---|---|---|---|---|---|---|---|---|---|---|---|---|---|---|
| | | | | 85 | | | | | 90 | | | | | 95 | |

| Glu | Thr | Val | Pro | Lys | Pro | Cys | Cys | Ala | Pro | Thr | Gln | Leu | Asn | Ala | Ile |
|---|---|---|---|---|---|---|---|---|---|---|---|---|---|---|---|
| | | | 100 | | | | | 105 | | | | | 110 | | |

| Ser | Val | Leu | Tyr | Phe | Asp | Asp | Ser | Ser | Asn | Val | Ile | Leu | Lys | Lys | Tyr |
|---|---|---|---|---|---|---|---|---|---|---|---|---|---|---|---|
| | | | 115 | | | | | 120 | | | | | 125 | | |

| Arg | Asn | Met | Val | Val | Arg | Ala | Cys | Gly | Cys | His |
|---|---|---|---|---|---|---|---|---|---|---|
| | 130 | | | | | 135 | | | | |

( 2 ) INFORMATION FOR SEQ ID NO:3:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..342

( x i ) SEQUENCE DESCRIPTION: SEQ ID NO:3:

```
CAA GCC AAA CAC AAA CAG CGG AAA CGC CTT AAG TCC AGC TGT AAG AGA         48
Gln Ala Lys His Lys Gln Arg Lys Arg Leu Lys Ser Ser Cys Lys Arg
 1               5                  10                  15

CAC CCT TTG TAC GTG GAC TTC AGT GAC GTG GGG TGG AAT GAC TGG ATT         96
His Pro Leu Tyr Val Asp Phe Ser Asp Val Gly Trp Asn Asp Trp Ile
             20                  25                  30

GTG GCT CCC CCG GGG TAT CAC GCC TTT TAC TGC CAC GGA GAA TGC CCT        144
Val Ala Pro Pro Gly Tyr His Ala Phe Tyr Cys His Gly Glu Cys Pro
         35                  40                  45

TTT CCT CTG GCT GAT CAT CTG AAC TCC ACT AAT CAT GCC ATT GTT CAG        192
Phe Pro Leu Ala Asp His Leu Asn Ser Thr Asn His Ala Ile Val Gln
     50                  55                  60

ACG TTG GTC AAC TCT GTT AAC TCT AAG ATT CCT AAG GCA TGC TGT GTC        240
Thr Leu Val Asn Ser Val Asn Ser Lys Ile Pro Lys Ala Cys Cys Val
 65                  70                  75                  80

CCG ACA GAA CTC AGT GCT ATC TCG ATG CTG TAC CTT GAC GAG AAT GAA        288
Pro Thr Glu Leu Ser Ala Ile Ser Met Leu Tyr Leu Asp Glu Asn Glu
                 85                  90                  95

AAG GTT GTA TTA AAG AAC TAT CAG GAC ATG GTT GTG GAG GGT TGT GGG        336
Lys Val Val Leu Lys Asn Tyr Gln Asp Met Val Val Glu Gly Cys Gly
            100                 105                 110

TGT CGC                                                                342
Cys Arg
```

( 2 ) INFORMATION FOR SEQ ID NO:4:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
             20                  25                  30

Val Ala Pro Pro Gly Tyr His Ala Phe Tyr Cys His Gly Glu Cys Pro
         35                  40                  45

Phe Pro Leu Ala Asp His Leu Asn Ser Thr Asn His Ala Ile Val Gln
     50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110
```

Cys Arg ( 2 ) INFORMATION FOR SEQ ID NO:5:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1224

( x i ) SEQUENCE DESCRIPTION: SEQ ID NO:5:

```
ATG ATT CCT GGT AAC CGA ATG CTG ATG GTC GTT TTA TTA TGC CAA GTC         48
Met Ile Pro Gly Asn Arg Met Leu Met Val Val Leu Leu Cys Gln Val
 1           5                  10                  15

CTG CTA GGA GGC GCG AGC CAT GCT AGT TTG ATA CCT GAG ACG GGG AAG         96
Leu Leu Gly Gly Ala Ser His Ala Ser Leu Ile Pro Glu Thr Gly Lys
              20                  25                  30

AAA AAA GTC GCC GAG ATT CAG GGC CAC GCG GGA GGA CGC CGC TCA GGG        144
Lys Lys Val Ala Glu Ile Gln Gly His Ala Gly Gly Arg Arg Ser Gly
         35                  40                  45

CAG AGC CAT GAG CTC CTG CGG GAC TTC GAG GCG ACA CTT CTG CAG ATG        192
Gln Ser His Glu Leu Leu Arg Asp Phe Glu Ala Thr Leu Leu Gln Met
     50                  55                  60

TTT GGG CTG CGC CGC CGC CCG CAG CCT AGC AAG AGT GCC GTC ATT CCG        240
Phe Gly Leu Arg Arg Arg Pro Gln Pro Ser Lys Ser Ala Val Ile Pro
 65                  70                  75                  80

GAC TAC ATG CGG GAT CTT TAC CGG CTT CAG TCT GGG GAG GAG GAG GAA        288
Asp Tyr Met Arg Asp Leu Tyr Arg Leu Gln Ser Gly Glu Glu Glu Glu
                 85                  90                  95

GAG CAG ATC CAC AGC ACT GGT CTT GAG TAT CCT GAG CGC CCG GCC AGC        336
Glu Gln Ile His Ser Thr Gly Leu Glu Tyr Pro Glu Arg Pro Ala Ser
                100                 105                 110

CGG GCC AAC ACC GTG AGG AGC TTC CAC CAC GAA GAA CAT CTG GAG AAC        384
Arg Ala Asn Thr Val Arg Ser Phe His His Glu Glu His Leu Glu Asn
            115                 120                 125

ATC CCA GGG ACC AGT GAA AAC TCT GCT TTT CGT TTC CTC TTT AAC CTC        432
Ile Pro Gly Thr Ser Glu Asn Ser Ala Phe Arg Phe Leu Phe Asn Leu
        130                 135                 140

AGC AGC ATC CCT GAG AAC GAG GCG ATC TCC TCT GCA GAG CTT CGG CTC        480
Ser Ser Ile Pro Glu Asn Glu Ala Ile Ser Ser Ala Glu Leu Arg Leu
145                 150                 155                 160

TTC CGG GAG CAG GTG GAC CAG GGC CCT GAT TGG GAA AGG GGC TTC CAC        528
Phe Arg Glu Gln Val Asp Gln Gly Pro Asp Trp Glu Arg Gly Phe His
                165                 170                 175

CGT ATA AAC ATT TAT GAG GTT ATG AAG CCC CCA GCA GAA GTG GTG CCT        576
Arg Ile Asn Ile Tyr Glu Val Met Lys Pro Pro Ala Glu Val Val Pro
            180                 185                 190

GGG CAC CTC ATC ACA CGA CTA CTG GAC ACG AGA CTG GTC CAC CAC AAT        624
Gly His Leu Ile Thr Arg Leu Leu Asp Thr Arg Leu Val His His Asn
        195                 200                 205

GTG ACA CGG TGG GAA ACT TTT GAT GTG AGC CCT GCG GTC CTT CGC TGG        672
Val Thr Arg Trp Glu Thr Phe Asp Val Ser Pro Ala Val Leu Arg Trp
    210                 215                 220

ACC CGG GAG AAG CAG CCA AAC TAT GGG CTA GCC ATT GAG GTG ACT CAC        720
Thr Arg Glu Lys Gln Pro Asn Tyr Gly Leu Ala Ile Glu Val Thr His
225                 230                 235                 240

CTC CAT CAG ACT CGG ACC CAC CAG GGC CAG CAT GTC AGG ATT AGC CGA        768
Leu His Gln Thr Arg Thr His Gln Gly Gln His Val Arg Ile Ser Arg
                245                 250                 255
```

| | | | | | | | | | | | | | | | | |
|---|---|---|---|---|---|---|---|---|---|---|---|---|---|---|---|---|
| TCG | TTA | CCT | CAA | GGG | AGT | GGG | AAT | TGG | GCC | CAG | CTC | CGG | CCC | CTC | CTG | 816 |
| Ser | Leu | Pro | Gln 260 | Gly | Ser | Gly | Asn | Trp 265 | Ala | Gln | Leu | Arg | Pro 270 | Leu | Leu | |
| GTC | ACC | TTT | GGC | CAT | GAT | GGC | CGG | GGC | CAT | GCC | TTG | ACC | CGA | CGC | CGG | 864 |
| Val | Thr | Phe 275 | Gly | His | Asp | Gly | Arg 280 | Gly | His | Ala | Leu | Thr 285 | Arg | Arg | Arg | |
| AGG | GCC | AAG | CGT | AGC | CCT | AAG | CAT | CAC | TCA | CAG | CGG | GCC | AGG | AAG | AAG | 912 |
| Arg | Ala 290 | Lys | Arg | Ser | Pro | Lys 295 | His | His | Ser | Gln | Arg 300 | Ala | Arg | Lys | Lys | |
| AAT | AAG | AAC | TGC | CGG | CGC | CAC | TCG | CTC | TAT | GTG | GAC | TTC | AGC | GAT | GTG | 960 |
| Asn 305 | Lys | Asn | Cys | Arg | Arg 310 | His | Ser | Leu | Tyr | Val 315 | Asp | Phe | Ser | Asp | Val 320 | |
| GGC | TGG | AAT | GAC | TGG | ATT | GTG | GCC | CCA | CCA | GGC | TAC | CAG | GCC | TTC | TAC | 1008 |
| Gly | Trp | Asn | Asp | Trp 325 | Ile | Val | Ala | Pro | Pro 330 | Gly | Tyr | Gln | Ala | Phe 335 | Tyr | |
| TGC | CAT | GGG | GAC | TGC | CCC | TTT | CCA | CTG | GCT | GAC | CAC | CTC | AAC | TCA | ACC | 1056 |
| Cys | His | Gly | Asp 340 | Cys | Pro | Phe | Pro | Leu 345 | Ala | Asp | His | Leu | Asn 350 | Ser | Thr | |
| AAC | CAT | GCC | ATT | GTG | CAG | ACC | CTG | GTC | AAT | TCT | GTC | AAT | TCC | AGT | ATC | 1104 |
| Asn | His | Ala 355 | Ile | Val | Gln | Thr | Leu 360 | Val | Asn | Ser | Val | Asn 365 | Ser | Ser | Ile | |
| CCC | AAA | GCC | TGT | TGT | GTG | CCC | ACT | GAA | CTG | AGT | GCC | ATC | TCC | ATG | CTG | 1152 |
| Pro | Lys 370 | Ala | Cys | Cys | Val | Pro 375 | Thr | Glu | Leu | Ser | Ala 380 | Ile | Ser | Met | Leu | |
| TAC | CTG | GAT | GAG | TAT | GAT | AAG | GTG | GTA | CTG | AAA | AAT | TAT | CAG | GAG | ATG | 1200 |
| Tyr 385 | Leu | Asp | Glu | Tyr | Asp 390 | Lys | Val | Val | Leu | Lys 395 | Asn | Tyr | Gln | Glu | Met 400 | |
| GTA | GTA | GAG | GGA | TGT | GGG | TGC | CGC | | | | | | | | | 1224 |
| Val | Val | Glu | Gly | Cys 405 | Gly | Cys | Arg | | | | | | | | | |

( 2 ) INFORMATION FOR SEQ ID NO:6:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met 1 | Ile | Pro | Gly | Asn 5 | Arg | Met | Leu | Met | Val 10 | Val | Leu | Leu | Cys | Gln Val 15 |
| Leu | Leu | Gly | Gly 20 | Ala | Ser | His | Ala | Ser 25 | Leu | Ile | Pro | Glu | Thr 30 | Gly Lys |
| Lys | Lys | Val 35 | Ala | Glu | Ile | Gln | Gly 40 | His | Ala | Gly | Gly | Arg 45 | Arg | Ser Gly |
| Gln | Ser | His 50 | Glu | Leu | Leu | Arg | Asp 55 | Phe | Glu | Ala | Thr | Leu 60 | Leu | Gln Met |
| Phe 65 | Gly | Leu | Arg | Arg | Arg 70 | Pro | Gln | Pro | Ser | Lys 75 | Ser | Ala | Val | Ile Pro 80 |
| Asp | Tyr | Met | Arg | Asp 85 | Leu | Tyr | Arg | Leu | Gln 90 | Ser | Gly | Glu | Glu | Glu 95 |
| Glu | Gln | Ile | His 100 | Ser | Thr | Gly | Leu | Glu 105 | Tyr | Pro | Glu | Arg | Pro 110 | Ala Ser |
| Arg | Ala | Asn 115 | Thr | Val | Arg | Ser | Phe 120 | His | His | Glu | Glu | His 125 | Leu | Glu Asn |
| Ile | Pro | Gly 130 | Thr | Ser | Glu | Asn | Ser 135 | Ala | Phe | Arg | Phe | Leu 140 | Phe | Asn Leu |
| Ser 145 | Ser | Ile | Pro | Glu | Asn 150 | Glu | Ala | Ile | Ser | Ser 155 | Ala | Glu | Leu | Arg Leu 160 |

```
Phe  Arg  Glu  Gln  Val  Asp  Gln  Gly  Pro  Asp  Trp  Glu  Arg  Gly  Phe  His
               165                      170                     175

Arg  Ile  Asn  Ile  Tyr  Glu  Val  Met  Lys  Pro  Pro  Ala  Glu  Val  Val  Pro
               180                      185                     190

Gly  His  Leu  Ile  Thr  Arg  Leu  Leu  Asp  Thr  Arg  Leu  Val  His  His  Asn
               195                      200                     205

Val  Thr  Arg  Trp  Glu  Thr  Phe  Asp  Val  Ser  Pro  Ala  Val  Leu  Arg  Trp
     210                         215                     220

Thr  Arg  Glu  Lys  Gln  Pro  Asn  Tyr  Gly  Leu  Ala  Ile  Glu  Val  Thr  His
225                      230                     235                          240

Leu  His  Gln  Thr  Arg  Thr  His  Gln  Gly  Gln  His  Val  Arg  Ile  Ser  Arg
                    245                      250                     255

Ser  Leu  Pro  Gln  Gly  Ser  Gly  Asn  Trp  Ala  Gln  Leu  Arg  Pro  Leu  Leu
               260                      265                     270

Val  Thr  Phe  Gly  His  Asp  Gly  Arg  Gly  His  Ala  Leu  Thr  Arg  Arg  Arg
               275                      280                     285

Arg  Ala  Lys  Arg  Ser  Pro  Lys  His  His  Ser  Gln  Arg  Ala  Arg  Lys  Lys
     290                         295                     300

Asn  Lys  Asn  Cys  Arg  Arg  His  Ser  Leu  Tyr  Val  Asp  Phe  Ser  Asp  Val
305                      310                     315                          320

Gly  Trp  Asn  Asp  Trp  Ile  Val  Ala  Pro  Pro  Gly  Tyr  Gln  Ala  Phe  Tyr
                    325                      330                     335

Cys  His  Gly  Asp  Cys  Pro  Phe  Pro  Leu  Ala  Asp  His  Leu  Asn  Ser  Thr
               340                      345                     350

Asn  His  Ala  Ile  Val  Gln  Thr  Leu  Val  Asn  Ser  Val  Asn  Ser  Ser  Ile
          355                      360                     365

Pro  Lys  Ala  Cys  Cys  Val  Pro  Thr  Glu  Leu  Ser  Ala  Ile  Ser  Met  Leu
     370                         375                     380

Tyr  Leu  Asp  Glu  Tyr  Asp  Lys  Val  Val  Leu  Lys  Asn  Tyr  Gln  Glu  Met
385                      390                     395                          400

Val  Val  Glu  Gly  Cys  Gly  Cys  Arg
                    405
```

(2) INFORMATION FOR SEQ ID NO:7:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Ser  Ala  Pro  Gly  Arg  Arg  Arg  Gln  Gln  Ala  Arg  Asn  Arg  Ser  Thr  Pro
1                    5                       10                      15

Ala  Gln  Asp  Val
               20
```

(2) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Ser  Xaa  Lys  His  Xaa  Xaa  Gln  Arg  Xaa  Arg  Lys  Lys  Asn  Asn  Asn
1              5                      10                          15
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Ser  Thr  Gly  Gly  Lys  Gln  Arg  Ser  Gln  Asn  Arg  Ser  Lys  Thr  Pro  Lys
1              5                        10                       15
Asn  Gln  Glu  Ala
            20
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Xaa  Val  Val  Leu  Lys  Asn  Tyr  Gln  Asp  Met  Val
1              5                        10
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Xaa  Xaa  Lys  Val  Val  Leu  Lys  Asn  Tyr  Gln  Asp  Met
1              5                        10
```

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Ser  Ala  Pro  Gly  Arg  Arg  Arg  Gln  Gln  Ala  Arg  Asn  Arg  Ser  Thr  Pro
1              5                        10                       15
Ala  Gln  Asp  Val
            20
```

( 2 ) INFORMATION FOR SEQ ID NO:13:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Asn  Pro  Glu  Tyr  Val  Pro  Lys  Xaa  Xaa  Xaa  Ala  Pro  Thr  Lys  Leu  Asn
1              5                        10                       15
Ala  Ile  Ser  Val
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Xaa Ala Thr Asn Xaa Ala Ile Val Gln Xaa Leu Val Xaa Leu Met
1               5                   10                  15
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Xaa Val Xaa Ala Xaa Gly
1               5
```

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Leu Tyr Leu Asp Glu Asn Glu Lys
1               5
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Val Val Glu Gly Xaa Gly Xaa Arg
1               5
```

( 2 ) INFORMATION FOR SEQ ID NO:18:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Leu Tyr Leu Asp Glu Asn Glu Lys Val Val Leu Lys Asn Tyr Gln Asp
1               5                   10                  15
Met Val Val Glu Gly Xaa Gly Xaa Arg
                20                  25
```

( 2 ) INFORMATION FOR SEQ ID NO:19:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: protein ( x i ) SEQUENCE DESCRIPTION: SEQ ID NO:19:

Ser Thr Gly Gly Lys Gln Arg Ser Gln Asn Arg Ser Lys Thr Pro Lys
1               5                   10                  15

Asn Gln Glu Ala
        20

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Xaa Ala Thr Asn His Ala Ile Val Gln Thr Leu Val His Phe Ile Asn
1               5                   10                  15

Xaa Glu Thr Val
        20

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

Leu Tyr Leu Xaa Glu Tyr Asp Xaa Val Val Leu Xaa Asn Tyr Gln
1               5                   10                  15

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

Ser Ala Xaa Xaa His Xaa Ile Val Gln Thr
1               5                   10

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Xaa Ala Thr Asn Xaa Ala Ile Val Gln Thr Leu
1               5                   10

( 2 ) INFORMATION FOR SEQ ID NO:24:

( i ) SEQUENCE CHARACTERISTICS:
   ( A ) LENGTH: 11 amino acids
   ( B ) TYPE: amino acid
   ( D ) TOPOLOGY: linear ( i i ) MOLECULE TYPE: protein ( x i ) SEQUENCE DESCRIPTION: SEQ ID NO:24:

Leu Tyr Leu Asp Glu Xaa Glu Xaa Val Val Leu
1               5                   10

( 2 ) INFORMATION FOR SEQ ID NO:25:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: protein ( x i ) SEQUENCE DESCRIPTION: SEQ ID NO:25:

Xaa Xaa Xaa Gly Arg Xaa Arg Gln
1               5

( 2 ) INFORMATION FOR SEQ ID NO:26:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO:26:

Xaa Xaa Gly Gly Xaa Gln Arg
1               5

( 2 ) INFORMATION FOR SEQ ID NO:27:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: protein ( x i ) SEQUENCE DESCRIPTION: SEQ ID NO:27:

Leu Tyr Leu Asp Xaa Asn Xaa Xaa Val Val Leu Xaa Asn
1               5                   10

( 2 ) INFORMATION FOR SEQ ID NO:28:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO:28:

Xaa Pro Glu Xaa Val Pro Xaa
1               5

( 2 ) INFORMATION FOR SEQ ID NO:29:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: protein ( x i ) SEQUENCE DESCRIPTION: SEQ ID NO:29:

Ser Ala Pro Gly Arg Arg Arg Gln Gln Ala Arg Asn Arg Ser Thr Pro
1               5                   10                  15

Ala Gln Asp Val
        20

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

Ser Thr Gly Gly Lys Arg Arg Ser Gln Asn Arg Ser Lys Thr Pro Lys
1               5                   10                  15

Asn Gln Glu Ala
        20

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

Ser Thr Gly Gly Lys Gln Arg Ser Gln Asn Arg
1               5                   10

( 2 ) INFORMATION FOR SEQ ID NO:32:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

WSNACNGGNG GNAARCARMG NWSNCARAAY MG        32

( 2 ) INFORMATION FOR SEQ ID NO:33:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

Asn His Ala Ile Val Gln Thr Leu Val His Phe Ile Asn
1               5                   10

( 2 ) INFORMATION FOR SEQ ID NO:34:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: misc difference
    ( B ) LOCATION: replace (18, 27, 30, 33, 39, 42, 45)
    ( D ) OTHER INFORMATION: note="All 'N's in this sequence
        designate the nucleotide analog deoxyinosinetriphosphate
        ( d I T P ) which was used in the positions where all four of
        the nucleotides (A, C, T or G) were possible."

( x i ) SEQUENCE DESCRIPTION: SEQ ID NO:34:

TTTTTTTTGG ATCCRTTNAT RAARTGNACN ARNGTYTGNA CNATNGCRTG RTT     53

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

Lys Thr Pro Lys Asn Gln Glu Ala Leu Arg
1               5                       10

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc difference
        ( B ) LOCATION: replace (3, 6, 9, 18, 24, 27)
        ( D ) OTHER INFORMATION: note="All 'N's in this sequence
            designate the nucleotide analog deoxyinosinetriphosphate
            ( d I T P ) which was used in the positions where all four of
            the nucleotides (A, C, T or G) were possible."

( x i ) SEQUENCE DESCRIPTION: SEQ ID NO:36:

AANACNCCNA ARAAYCANGA RGCNYTNMG     29

( 2 ) INFORMATION FOR SEQ ID NO:37:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GAGCAAGTTC AGCCTGGTTA AGTCC     25

( 2 ) INFORMATION FOR SEQ ID NO:38:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

TGGCTTATGA GTATTTCTTC CAGGG     25

( 2 ) INFORMATION FOR SEQ ID NO:39:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:39:

GTCGCTGCTG CTGTTCTCTG CCACGTTGGC    30

( 2 ) INFORMATION FOR SEQ ID NO:40:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:40:

GAATTCGTCG ACATGCACGT GCGCTCA    27

( 2 ) INFORMATION FOR SEQ ID NO:41:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:41:

CCATGGCGTT GTACAGGTCC AG    22

( 2 ) INFORMATION FOR SEQ ID NO:42:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: protein ( x i ) SEQUENCE DESCRIPTION: SEQ ID NO:42:

Gln Ala Lys His Lys Gln Arg Lys Arg
1                   5

( 2 ) INFORMATION FOR SEQ ID NO:43:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:43:

CAAGCCAAAC ACAAACAGCG GAAACGC    27

( 2 ) INFORMATION FOR SEQ ID NO:44:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:44:

AAGCTTCCGC GGCTAGCGAC ACCCACAACC CTCCACA    37

( 2 ) INFORMATION FOR SEQ ID NO:45:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

ACTGTCGACA TGGTGGCCGG GACCCG    26

( 2 ) INFORMATION FOR SEQ ID NO:46:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

ACGTTTTTCT CTTTTGTGGA GAGGAT    26

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

TGAAGCGGCC GCAACAGACG T    21

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

CTGTTGCGGC CGCTTCAACG T    21

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

Met Ile Pro Gly Asn Arg Met Leu
    1               5

( 2 ) INFORMATION FOR SEQ ID NO:50:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

GAATTCGTCG ACATGATTCC TGGTACCGAA TGCTGA        36

( 2 ) INFORMATION FOR SEQ ID NO:51:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

Val  Glu  Gly  Cys  Gly  Cys  Arg
    1                   5

( 2 ) INFORMATION FOR SEQ ID NO:52:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

AAGCTTCCGC GGCTCAGCGG CACCCACATC CCTCTACT        38

( 2 ) INFORMATION FOR SEQ ID NO:53:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

ACTACCGCGG TAAATGAGTG CGACGG        26

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

CACTGCATTC TAGTTGTGGT        20

( 2 ) INFORMATION FOR SEQ ID NO:55:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear (ii) MOLECULE TYPE: cDNA (xi) SEQUENCE DESCRIPTION: SEQ ID NO:55:

CAAGCCAAAC ACAAACAGCG GAAACGC 27

(2) INFORMATION FOR SEQ ID NO:56:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:56:

AAGCTTCCGC GGCTAGCGAC ACCCACAACC CTCCACA 37

(2) INFORMATION FOR SEQ ID NO:57:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:57:

TCCACGGGGA GCAAACAGCG CA 22

(2) INFORMATION FOR SEQ ID NO:58:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:58:

CATACCGCGG AGCTAGTGGC AGCCACA 27

(2) INFORMATION FOR SEQ ID NO:59:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:59:

GAATTCGTCG ACATGATTCC TGGTAACCGA ATGCTGA 37

(2) INFORMATION FOR SEQ ID NO:60:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:60:

ACGCTTGGCC CTCCGGCGTC GGGTCAA 27

(2) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

TTTTTCCAG TCTTTTGGAC ACCAGGTTGG         30

(2) INFORMATION FOR SEQ ID NO:62:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

AAGCTTCCGC GGCTAGCGAC ACCCACAACC CTCCACA 37

(2) INFORMATION FOR SEQ ID NO:63:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

Val Glu Gly Cys Gly Cys Arg
1               5

What is claimed is:

1. A method of producing an osteogenic protein preparation comprising a heterodimer of a first polypeptide subunit and a second polypeptide subunit comprising the step of culturing in a suitable culture media a cell line transformed with a first and a second nucleotide sequence, said first nucleotide sequence being selected from the group consisting of:
    the nucleotide sequence as shown in SEQ ID NO: 3; and
    a nucleotide sequence which encodes the same sequence of amino acids as encoded by the nucleotide sequence shown in SEQ ID NO: 3;
and said second nucleotide sequence being selected from the group consisting of:
    the nucleotide sequence as shown in SEQ ID NO: 1; and
    a nucleotide sequence which encodes the same sequence of amino acids as encoded by the nucleotide sequence shown in SEQ ID NO: 1;
to produce said heterodimer.

2. The method of claim 1 wherein said polypeptide subunits are expressed by means of a heterologous pre-pro sequence.

3. The method of claim 1 wherein said cell line is selected from the group consisting of mammalian, bacterial, insect and yeast cell lines.

4. The method of claim 1 wherein said cell line is Chinese hamster ovary cell lines.

5. The method of claim 1 wherein said heterodimer is isolated from the culture medium according to the steps of (a) subjecting said culture medium to a series of chromatography steps utilizing a Q-Sepharose column, an S-Sepharose column and a Phenyl-Sepharose column to recover an active fraction and (b) subjecting the active fraction to reverse phase chromatography using a C-18 high performance liquid chromatography column equilibrated with buffers containing trifluoroacetic acid and acetonitrile by eluting the active preparation at concentrations between 35% and 45% acetonitrile.

6. A cell transformed with purified and isolated nucleic acids comprising a first and a second nucleotide sequence, said first nucleotide sequence being selected from the group consisting of:
    the nucleotide sequence as shown in SEQ ID NO: 3; and
    a nucleotide sequence which encodes the same sequence of amino acids as encoded by the nucleotide sequence shown in SEQ ID NO: 3;
and said second nucleotide sequence being selected from the group consisting of:
    the nucleotide sequence as shown in SEQ ID NO: 1; and
    a nucleotide sequence which encodes the same sequence of amino acids as encoded by the nucleotide sequence shown in SEQ ID NO: 1.

7. A method of preparing a cell line capable of producing an osteogenic protein preparation comprising a heterodimer of a first polypeptide subunit and a second polypeptide subunit comprising the step of transforming a cell line with a first and a second nucleotide sequence, said first nucleotide sequence being selected from the group consisting of:

the nucleotide sequence as shown in SEQ ID NO: 3; and a nucleotide sequence which encodes the same sequence of amino acids as encoded by the nucleotide sequence shown in SEQ ID NO: 3;

and said second nucleotide sequence being selected from the group consisting of:

the nucleotide sequence as shown in SEQ ID NO: 1; and a nucleotide sequence which encodes the same sequence of amino acids as encoded by the nucleotide sequence shown in SEQ ID NO: 1.

8. The method according to claim 7 comprising a first step in which said cell line is transformed with one of said first and second nucleotide sequences and a second step in which said cell line is transformed with the other of said first and second nucleotide sequences.

9. The method according to claim 7 wherein said cell line is transformed with a vector comprising both said first and said second nucleotide sequences.

10. A expression vector comprising a first and a second nucleotide sequence said first nucleotide sequence being selected from the group consisting of:

the nucleotide sequence as shown in SEQ ID NO: 3; and a nucleotide sequence which encodes the same sequence of amino acids as encoded by the nucleotide sequence shown in SEQ ID NO: 3;

and said second nucleotide sequence being selected from the group consisting of:

the nucleotide sequence as shown in SEQ ID NO: 1; and a nucleotide sequence which encodes the same sequence of amino acids as encoded by the nucleotide sequence shown in SEQ ID NO: 1.

* * * * *

UNITED STATES PATENT AND TRADEMARK OFFICE
CERTIFICATE OF CORRECTION

PATENT NO. : 5,284,756

DATED : February 8, 1994

INVENTOR(S) : Grinna et al.

It is certified that error appears in the above-identified patent and that said Letters Patent is hereby corrected as shown below:

Column 2, line 18, "Weight" should be --weight--.

Column 3, line 67, "p3" should be --P3--.

Column 5, line 10, after "NOS:" insert --1--.

Column 13, line 51, "of" should be --OF--.

Column 13, line 67, "of" should be --OF--.

Column 13, line 67, "Were" should be --were--.

Column 18, line 42, "Ampli-Tag" should be --Ampli-Taq--.

Column 18, line 53, "mmmbrane" should be --membrane--.

Column 19, line 28, "TGI" should be --TG1--.

Column 22, line 55, "NNA" should be --RNA--.

Column 23, line 21, "BolII" should be --BglII--.

Column 23, line 23, "BolII" should be --BglII--.

Column 24, line 45, "BolII" should be --BglII--.

UNITED STATES PATENT AND TRADEMARK OFFICE
CERTIFICATE OF CORRECTION

PATENT NO. : 5,284,756

DATED : February 8, 1994

INVENTOR(S) : Grinna et al.

It is certified that error appears in the above-identified patent and that said Letters Patent is hereby corrected as shown below:

Column 24, line 48, "BolII" should be --BglII--.

Column 25, line 59, after "streptomycin" insert --(--.

Column 27, line 29, "(ING3918)" should be --(pING3918)--.

Column 29, line 19, "(C11131)" should be --(C1131)--.

Signed and Sealed this

Twenty-fifth Day of October, 1994

Attest:

BRUCE LEHMAN

Attesting Officer     Commissioner of Patents and Trademarks